United States Patent
Aime et al.

(10) Patent No.: US 10,369,236 B2
(45) Date of Patent: Aug. 6, 2019

(54) PROCESS FOR THE PREPARATION OF HYPERPOLARIZED CARBOXYLATE COMPOUNDS

(71) Applicant: BRACCO IMAGING S.P.A., Milan (IT)

(72) Inventors: Silvio Aime, Carignano (IT); Tommaso Boi, Borgo San Dalmazzo (IT); Erika Cerutti, Bra (IT); Francesca Reineri, Cuneo (IT)

(73) Assignee: BRACCO IMAGING S.P.A., Milan (IT)

( * ) Notice: Subject to any disclaimer, the term of this patent is extended or adjusted under 35 U.S.C. 154(b) by 451 days.

(21) Appl. No.: 15/031,860

(22) PCT Filed: Oct. 27, 2014

(86) PCT No.: PCT/EP2014/072983
§ 371 (c)(1),
(2) Date: Apr. 25, 2016

(87) PCT Pub. No.: WO2015/063020
PCT Pub. Date: May 7, 2015

(65) Prior Publication Data
US 2016/0263256 A1 Sep. 15, 2016

Related U.S. Application Data

(63) Continuation of application No. PCT/EP2014/072983, filed on Oct. 27, 2014.

(30) Foreign Application Priority Data

Oct. 28, 2013 (EP) .................................. 13190409

(51) Int. Cl.
*A61B 5/055* (2006.01)
*A61K 51/04* (2006.01)
*A61K 49/10* (2006.01)
*C07C 67/283* (2006.01)
*C07C 69/155* (2006.01)
*C07C 69/716* (2006.01)
*C07C 227/20* (2006.01)
*C07C 231/12* (2006.01)
*C07C 233/47* (2006.01)
*C07C 51/41* (2006.01)
*C07C 69/14* (2006.01)
*B01J 31/24* (2006.01)
*C07C 51/09* (2006.01)
*C07C 69/68* (2006.01)
*G01R 33/56* (2006.01)

(52) U.S. Cl.
CPC .......... *A61K 51/0402* (2013.01); *A61B 5/055* (2013.01); *A61K 49/10* (2013.01); *B01J 31/2404* (2013.01); *C07C 51/09* (2013.01); *C07C 51/412* (2013.01); *C07C 67/283* (2013.01); *C07C 69/14* (2013.01); *C07C 69/155* (2013.01); *C07C 69/68* (2013.01); *C07C 69/716* (2013.01); *C07C 227/20* (2013.01); *C07C 231/12* (2013.01); *C07C 233/47* (2013.01); *G01R 33/5601* (2013.01); *B01J 2531/822* (2013.01); *C07B 2200/05* (2013.01)

(58) Field of Classification Search
None
See application file for complete search history.

(56) References Cited

U.S. PATENT DOCUMENTS

| | | |
|---|---|---|
| 3,615,723 A | 10/1971 | Meade |
| 5,334,791 A | 8/1994 | Cavell et al. |
| 6,574,495 B1 | 6/2003 | Golman et al. |
| 6,872,380 B2 | 3/2005 | Axelsson et al. |
| 8,961,933 B2 | 2/2015 | Reineri et al. |
| 2011/0095759 A1 | 4/2011 | Bhattacharya |

FOREIGN PATENT DOCUMENTS

| | | |
|---|---|---|
| CN | 1306441 A | 8/2001 |
| EP | 1548454 A1 | 6/2006 |
| JP | 2000-513979 A | 10/2000 |
| JP | 2001-522819 A | 11/2001 |
| JP | 2003-500369 A | 1/2003 |
| WO | 1998-001766 A1 | 1/1998 |
| WO | 1999-024080 A1 | 5/1999 |
| WO | 2007-044867 A | 4/2007 |
| WO | 2009-124250 A1 | 10/2009 |
| WO | 2010-037771 A1 | 4/2010 |

OTHER PUBLICATIONS

Goldman et al. (Mag. Reson. Imag. 2005, 23, 153-157).*
Heaney et al. (Org. Biomol. Chem. 2003, 1, 4302-4316).*
Office Action for Chinese application No. 2014800589870, dated May 22, 2017 (with English translation).
PCT International Preliminary Report on Patentability for PCT application No. PCT/EP2014/072983, dated May 3, 2016.
Adams, Ralph W. et al., "Reversible Interactions with para-Hydrogen Enhance NMR Sensitivity by Polarization Transfer", Science, 2009, vol. 323, No. 5922, pp. 1708-1711, doi:10.1126/science.1168877, Edinburgh Research Explorer.
Aime, S. et al., "Para-Hydrogenation of unsaturated moieties on poly(lysine) derived substrates for teh development of novel hyperpolarized MRI contrast agents", Organic and Biomolecular Chemistry, vol. 3, No. 21, Nov. 7, 2005, pp. 3948-3954, XP002538146.
Albers, Mark J. et al., Hyperpolarized 13C Lactate, Pyruvate, and Alanine: Noninvasive Biomarkers for Prostate Cancer Detection and Grading, Cancer Research, 2008, vol. 68, No. 20, pp. 8607-8615, American Association for Cancer Research, www.aacrjournals.org.

(Continued)

Primary Examiner — Michael G. Hartley
Assistant Examiner — Melissa J Perreira
(74) Attorney, Agent, or Firm — Vivicar Law, PLLC

(57) ABSTRACT

The present invention relates to a process for the preparation of aqueous solutions of [1-$^{13}$C]-hyperpolarized carboxylate containing molecules of diagnostic interest that comprises parahydrogenating with molecular parahydrogen unsaturated alkenyl or alkynyl esters of the concerned $^{13}$C-carboxylate molecules.

19 Claims, 7 Drawing Sheets

(56) References Cited

OTHER PUBLICATIONS

Altes, Talissa A. et al., "Hyperpolarized Gas MR Imaging of the Lung", Symposium, J. Thorac Imaging, 2004, vol. 19, No. 4, pp. 250-258, Lippincott Williams & Wilkins.
Bargon, J. et al., "Parahydrogen-Induced Hyperpolarization of 15N", Proc. Intl. Soc. Mag. Reson. Med., 2007, vol. 15, p. 1317.
Barkemeyer, Jens et al., Hetero-NMR Enhancement via Parahydrogen Labeling, J. Am. Chem. Soc., 1995, vol. 117, No. 10, pp. 2927-2928, American Chemical Society.
Bhattacharya, Pratip et al., "Towards hyperpolarised 13C-succinate imaging of brain cancer", Journal of Magnetic Resonance, 2007, vol. 186, No. 1, pp. 150-155, XP022056087, Academic Press, Orlando, FL, US, ISSN: 1090-7807, DOI: 10.1016/j.jmr.2007.01.017.
Bowen, Sean et al., "Formulation and utilization of choline based samples for dissolution dynamic nuclear Solarization", Journal of Magnetic Resonance, 2013, vol. 236, pp. 26-30, XP055117610, Academic Press, Orlando, FL, US, ISSN: 1090-7807, DOI: 10.1016/j.jmr.2013.08.007.
Bowers, Clifford R., "Sensitivity Enhancement Utilizing Parahydrogen", Encyclopedia of nuclear magnetic resonance, 2002, vol. 9, Wiley, Chichester, New York, ISBN: 0471490822, pp. 750-770.
Brossat, Maude et al., "Development of an Acid-Washable Tag for the Separation of Enantioemers from Bioresolutions", Organic Process Research & Development, 2009, vol. 13, No. 4, pp. 706-709, American Chemical Society, doi:10.1021/op900028d.
Eisenberg, Richard et al., "Parahydrogen-Induced Polarization and Polarization Transfer in Hydrogenation and Oxidative Addition Reactions: A Mechanistic Probe", Advances in Chemistry, Chapter 4: Homogeneous Transition Metal Catalyzed Reactions, 1992, American Chemical Society, doi: 10.102/ba-1992-0230.ch.004, pp. 47-74.
Goldman, M. et al., "Hyperpolarization of 13C thruogh order transfer from parahydrogen: A new contrast agent for MRI", Magnetic Resonance Imaging, Elsevier Science, Tarrytown, NY, US, Feb. 1, 2005, vol. 23, No. 2, pp. 153-157, XP004843472, ISSN: 0730-725X.
Goldman, Maurice et al., "Conversion of a proton pair para order into 13C polarization by rf irradiation, for use in MRI", C. R. Physique, 2005, vol. 6, pp. 575-581, www.sciencedirect.com, Elsevier SAS, doi:10.1016/j.crhy.2005.03.002.
Goldman, M. et al., "Design and implementation of 13C hyper polarization from para-hydrogen, for new MRI contrast agents", Comptes Rendus-Chimie, Elsevier, Paris, FR, Mar. 1, 2006, vol. 9, No. 3-4, pp. 357-363, XP024979705, ISSN: 1631-0748.
Golman, K. et al., "Molecular imaging using hyperpolarized 13C", The British Journal of Radiology 2003, vol. 76 Spec. No. 2, 2003, pp. S118-S127, XP002538147, ISSN: 0007-1285.
Golman, K. et al., "Parahydrogen-Induced Polarization in Imaging: Subsecond 13C Angiography", Magnetic Resonance in Medicine, Wiley-Liss, Inc., 2001, vol. 46, pp. 1-5.
Golman, Klaes et al., "Real-time metabolic imaging", PNAS, 2006, vol. 103, No. 30, pp. 11270-11275, www.pnas.org/cgi/doi/10.1073/pnas.0601319103.
Grant, A.K. et al, "Early Experience with Simple Methods for Parahydrogen-Induced Hyperpolarization", : Proc. Intl. Soc. Mag. Reson. Med., 2006, v14, p. 2552.
Hovener, Jan-Bernd et al., "PASADENA hyperpolarization of 13C biomolecules: equipment design and installation", Magnetic Resonance Materials in Physics, Biology and Medicine 200904 DE, 2009, vol. 22, No. 2, pp. 111-121, XP002538149, ISSN: 0968-5243.
Hovener, Jan-Bernd et al., "Quality assurance of PASADENA hyperpolarization for 13C biomolecules", Magn Reson Mater Phy, 2009, vol. 22, pp. 123-134, doi:10.1007/s10334-008-0154-y, Springer.
Johannesson, Haukur et al., "Highly polarized nuclear spin systems and dipolar interactions in NMR: Transfer of para-hydrogen spin order into polarization by diabatic field cycling", C.R. Physique, 2004, vol. 5, pp. 315-324, Elsevier SAS, doi:10.1016/j.crhy.2004.02.001, www.sciencedirect.com.
Jonischkeit, Thorsten et al., "Generating long-lasting 1H and 13C hyperpolarization in small molecules with parahydrogen-indued polarization", The Journal of Chemical Physics, 2006, vol. 124, doi: 10.1063/1.2209235, AIP Publishing LLC, pp. 201109-1-201109-5.
Joo, F., "Aqueous biphasic hydrogenations", Accounts of Chemical Research Sep. 2002, vol. 35, No. 9, Sep. 2002, pp. 738-745, XP002538144, ISSN: 0001-4842.
Kohler, S.J. et al., "In Vivo 13Carbon Metabolic Imaging at 3T With Hyperpolarized 13C-1-Pyruvate", Magnetic Resonance in Medicine, 2007, vol. 58, No. 1, pp. 65-69, XP055117384, Wiley-Liss, Wilmington, DE, US, ISSN: 0740-3194, DOI: 10.1002/mrm.21253.
Koptyug, Igor V. et al., "para-Hydrogen-Induced Polarization in Heterogeneous Hydrogenation Reactions", J. Am. Chem. Soc., 2007, vol. 129, No. 17, pp. 5580-5586.
Kurdzesau, F. et al., "Dynamic nuclear polarization of small labelled molecules in frozen water-alcohol solutions", Journal of Physics D: Applied Physics, 2008, vol. 41, No. 15, p. 155506, XP020140635, Institute of Physics Pulishing Ltd., Bristol, GB, ISSN: 0022-3727.
Mansson, Sven et al., "13C imaging—a new diagnostic platform" Eur Radiol, 2006, vol. 16, pp. 57-67, doi:10.1007/500330-005-2806-x, Springer-Verlag.
Nelson, S.J. et al., "DNP-Hyperpolarized 13C Magnetic Resonance Metabolic Imaging for Cancer Applications", Applied Magnetic Resonance, 2008, vol. 34, pp. 533-544, doi:10.1007/s00723-008-0136-2, Springer-Verlag, The Netherlands.
Oros, Ana-Maria et al., "Hyperpolarized xenon in NMR and MRI", Phys. Med. Biol., 2004, vol. 49, pp. R105-R153, Institute of Physics Publishing Ltd, doi:10.1088/0031-9155/49/20/R01.
Reineri, F. et al., "New hyperpolarized contrast agents for 13C-MRI from para-hydrogenation of oligooxyethylenic alkynes", Journal of the American Chemical Society 20081112 American Chemical Society US, vol. 130, No. 45, Nov. 12, 2008, pp. 15047-15053, XP002538148.
Shchepin, Roman V. et al., "Pasadena hyperpolarised 13C Phospholactate", Journal of the American Chemical Society, 2012, vol. 134, No. 9, pp. 3957-3960, XP055117461, American Chemical Society Publications, Washington, DC, US, ISSN: 0002-7863, DOI: 10.1021/ja210639c.
Wang, C. et al., "Broader, greener, and more efficient: recent advances in asymmetric transfer hydrogenation", Chemistry, An Asian Journal Oct. 6, 2008, vol. 3, No. 10, Aug. 27, 208, pp. 1750-1770, XP002538145, ISSN: 1861-471X.
European Search Report for European application No. 13190409.6, dated May 21, 2014.
PCT International Search Report & Written Opinion of the International Searching Authority for PCT/EP2009/062674, dated Mar. 2, 2010.
PCT International Search Report and Written Opinion of the International Searching Authority for PCT application No. PCT/EP2014/072983, dated Jan. 21, 2015.
Office Action for Chinese application No. 200980138851.X, dated Apr. 27, 2012 (English translation).
Office Action for Chinese application No. 200980138851.X, dated Nov. 9, 2012 (English translation).
Office Action for Chinese application No. 200980138851.X, dated Jul. 23, 2013 (English translation).
Office Action for Chinese application No. 200980138851.X, dated Feb. 3, 2015 (English translation).
Office Action for European application No. 09783592.0, dated Feb. 24, 2014.
Office Action for European application No. 09783592.0, dated Feb. 15, 2016.
Office Action for Israeli application No. 212117, dated Jan. 27, 2014 (English translation per agent's reporting letter).
Office Action for Israeli application No. 212117, dated Mar. 19, 2015 (English translation per agent's reporting letter).
Office Action: Notification of Reasons for Refusal for Japanese application No. 2011-529542, dated Oct. 8, 2013.
Office Action for Chinese application No. 2014800589870, dated Mar. 21, 2018 (English translation).

* cited by examiner a)

b)

c)

a)

b)

c)

PROCESS FOR THE PREPARATION OF HYPERPOLARIZED CARBOXYLATE COMPOUNDS

CROSS-REFERENCE TO RELATED APPLICATIONS

This application is the national stage application of corresponding International Application Number PCT/EP2014/072983, filed Oct. 27, 2014, which claims priority to and the benefit of European Application Number EP13190409.6, filed Oc. 28, 2013, all of which are hereby incorporated by reference in their entirety.

FIELD OF THE INVENTION

The present invention generally relates to the field of Magnetic Resonance Imaging (MRI). More particularly, the invention relates to a process using the Para Hydrogen Induced Polarisation (PHIP) technique for the preparation of [1-$^{13}$C]-hyperpolarized carboxylate compounds of diagnostic interest as MR metabolic probes.

STATE OF THE ART

Magnetic Resonance Imaging is a well established powerful tool for medical and biological investigations both in vitro and in vivo. The main drawback of this technique is due to the intrinsic low sensitivity of the NMR spectroscopy on which MRI is based. In fact, the intensity of NMR signals depends on the difference between the nuclear spin states populations of the imaging nuclei. According to the well known Boltzman equation ($\Delta N = \gamma h B_0/(2\pi kT)$), this difference is a function of temperature and applied magnetic field, and, at thermal equilibrium, it is in the order of $10^{-5}$, i.e. very low.

The use of hyperpolarized molecules has been recently proposed as a possible solution of the said drawback and, in recent years, many efforts have been devoted to the development of both feasible and effective MR-hyperpolarization procedures.

Driving force in the recorded development stems in the potential this technique offer to overcome the sensitivity limitations of conventional MR Imaging opening a number of innovative applications both in chemistry and, especially, in biology.

Indeed, the significant improvement of the signal strength enabled by this technique for detectable compounds representing key molecules in the metabolic processes led to the development of innovative MR procedures exploiting the detection of key metabolites that directly report on specific steps of cellular processes (metabolic imaging). For instance, in vivo imaging has been performed using a suitably hyperpolarized metabolic substance, and real time imaging of metabolism has been observed with pyruvate 1-$^{13}$C-labeled as metabolic marker (see, for instance, Goldman K. et al, *Real time metabolic imaging*. PNAS 2006, 103 (30), 11270-11275) strongly suggesting the possible advantageous use of this (and other) key metabolite in the in vivo tumor diagnosis by means of hyperpolarized $^{13}$C Magnetic Resonance (MR) imaging (Albers M J. et al., *Hyperpolarized 13C lactate, pyruvate, and alanine: noninvasive biomarkers for prostate cancer detection and grading*; Cancer Research 2008, 68(20): 8607-15).

At the same time, the development of methods for $^{13}$C hyperpolarization has opened a new field in in vivo perfusion studies using $^{13}$C labeled hyperpolarized molecules (Mansson, S. et al, Eur. Radiol., 2006, 16, 57-67).

To this extent, the most used hyperpolarization approach relies on the application of Dynamic Nuclear Polarization (DNP) procedure that consists, essentially, in the following steps: i) preparation of a solid glassy solution of the substrate of interest with a stable organic radical; ii) bringing the solid solution to low temperature (close to 1K) into a magnet and irradiation at the frequency of the electron paramagnetic resonance (e.p.r.) transition of the organic radical for several minutes in order to transfer the electron polarization to the NMR active nuclei of the substrate molecules; iii) quick dissolution of the hyperpolarized material; iv) administration of the hyperpolarized molecules in vivo and NMR or image acquisition to report about their distribution and metabolic transformation.

Several metabolites have been polarized by means of DNP-dissolution method, among them pyruvate, acetate, fumarate, glutamate and many other metabolically interesting molecules. Commonly, the detected resonance is that of the $^{13}$C carbon atom of the carboxylate moiety, having a T1 value in the range of 20-60 s.

Overall, albeit the possibility to hyperpolarize, in principle, any substrate, the DNP-dissolution method requires sophisticated and expensive equipment. Another drawback of this technique is represented by the long polarization cycles, of about 1 hour, that are needed to reach a satisfactory nuclear polarization.

The alternative ParaHydrogen Induced Polarization (PHIP) method relies in the addition of a para-hydrogen (or parahydrogen, as herein used interchangeably) molecule to an unsaturated substrate, that allows to transform the spin order of the parahydrogen into hyperpolarization of heteronuclei.

Unlike the DNP method, the hyperpolarization procedure based on the use of parahydrogen is quite easy to handle and requires simple equipment, and offers faster preparations with hyperpolarization cycles as short as 1 min. by yielding signal-to-noise enhancements of up to $10^5$ with only little technical effort.

A bottleneck in the use of this technique is rather represented by the limited availability of relevant unsaturated molecular precursors that are necessary for molecular addition of parahydrogen acting, as said, as a source of spin order.

Optimal substrate precursors for preparing $^{13}$C or $^{15}$N hyperpolarized molecules (to be considered as preferable for in in vivo applications by having about zero background signal and longer relaxation times T1, consenting to limit the polarization loss due to relaxation) consist of unsaturated —C=C— or —C≡C— bonds adjacent to the heteronucleus to be polarized. For $^{13}$C compounds, this represents a three carbon limitation successfully represented, for instance, by the acrylate moiety leading, after parahydrogenation, to propionate compounds finding useful application for angiographic imaging (Goldman, M. et al., *C. R. Phys.* 2005, 6, 575-581). However, the need of suitable substrates including a hydrogenable double or triple bonds has, in practice, strongly limited the number of hyperpolarized molecules obtainable by use of this polarization technique.

Another issue contributing to further reduce attractive unsaturated precursors is represented by the instability due to a steady intramolecular re-arrangement thereof, the so called keto-enol tautomerism, converting vinyl alcohols to the corresponding aldehydes. The PHIP parahydrogenation of an enol form stabilized by formation of a phosphate, namely phosphoenolpyruvate that forms, after parandyrogen addition, hyperpolarized phospholactate is reported by Chekmenev et al. for instance in J. Am. Chem. Soc. 2012, 134, 3957-3960.

More recently, a new way to obtain hyperpolarized molecules by means of parahydrogen, called SABRE, has been introduced that allows to achieve polarization on molecules by reversible formation of ternary adducts of the hyperpolarization substrate, parahydrogen and an organometallic complex. (Adams, R. W. et al., Science 2009. 323, 17081711). This method allows to achieve polarization on molecules without that the hydrogen addition takes place, so one of the main limits of PHIP application can be circumvented.

Furthermore, a one-step method to obtain aqueous solution of parahydrogenated molecules which relies on the parahydrognation, in organic phase, of an alkenylic or alkynylic precursor of the desired hyperpolarized alkylic or alkenylic product, followed by its quick transformation into the final molecule and extraction in an aqueous phase is disclosed by the Applicant in WO 2010/037771. By using of this method, an aqueous solution of succinic acid has been, for instance, obtained by parahydrogenation of maleic anhydride in chloroform/acetone mixture, followed by dilution with basic aqueous solution and phase transfer.

However, at the best of our knowledge, $^{13}$C-hyperpolarized molecules of diagnostic interest, such as, especially, $^{13}$C-hyperpolarized acetate and pyruvate, are currently only available with DNP hyperpolarization technique (Kohler, S. J. et al.; Magn Reson. Med. 2007, 58, 6569), while their preparation with PHIP technique is deemed highly challenging, if not unfeasible (see the aforementioned J. Am. Chem. Soc. 2012, 134, 3957-3960).

SUMMARY OF THE INVENTION

Suitable unsaturated substrates and a preparation procedure have been now identified, herein disclosed, allowing to obtain [1-$^{13}$C]-hyperpolarized carboxylate containing molecules of diagnostic interest that are not directly obtainable with PHIP technique by addition of para-hydrogen to their one unsaturated direct precursor and are thus currently obtained by means of the DNP hyperpolarization technique.

In particular, an alternative PHIP-based polarization process is herein proposed that comprises using appropriate unsaturated esters, herein identified, as suitable hydrogenable substrate precursors for preparing [1-$^{13}$C]-hyperpolarized carboxylate containing molecules of diagnostic interest.

According to the proposed process, a suitable unsaturated ester of the carboxylate molecule of interest is obtained and hydrogenated with molecular para-hydrogen, thereby giving to the corresponding parahydrogenated ester; a polarization transfer is then induced from added H atoms to the $^{13}$C signal of the carboxylate carbon atom by known means, for instance trough application of a field cycling, yielding the [1-$^{13}$C]-hyperpolarized hydrogenated ester that is converted, by removal of the hydrogenated group, into the desired [1-$^{13}$C]-hyperpolarized free carboxylate molecule, that is finally collected in an aqueous solution as such, or in the protonated form, as the corresponding carboxylic acid.

Carboxylate containing molecules of diagnostic interest according to the invention are both the carboxylate compounds finding suitable application as MR probes in Magnetic Resonance Imaging (MRI) or Magnetic Resonance Spectroscopy (MRS), typically in vascular imaging, perfusion mapping, interventional imaging or molecular imaging, and the carboxylate molecules that are key part of biologic processes and metabolic pathways such as, for instance, tricarboxylic acid (TCA) cycle (also known as citric acid cycle), glycolysis, beta-oxidation, urea cycle and ketobody metabolic pathways, that find, instead, an always increasing use as metabolic MR markers.

Optimal unsaturated esters for the use of the invention, namely as suitable hydrogenable substrate precursor of the above carboxylate containing molecule, are vinyl esters, which have the $^{13}$C carboxylate carbon atom at the desirable three bond distance from the proton added with para-hydrogenation of the vinyl group.

However, due to the impossibility to easily have suitable ethenol or ethynol alcohol because of the keto-enolic equilibrium, a convenient preparation of the appropriate vinyl ester of carboxylate molecule of interest is sometime hardly feasible, as is the case, for instance, of the pyruvate, or impractical on a scale consenting to satisfy an always increasing medical demand.

We have now unexpectedly seen that, despite this involve moving the hydrogenable unsaturation at a distance from $^{13}$C carboxylate carbon atom exceeding the optimal three bond conventionally used and recommended as necessary to have a satisfactory polarization transfer, a different family of unsaturated esters, for instance including allyl and propargyl esters, can be conveniently prepared and used as suitable hydrogenable precursor molecules allowing to get the corresponding [1-$^{13}$C]-hyperpolarized carboxylate molecules of interest, or the corresponding carboxylic acid, with good yield and satisfying polarization degree, that has proven to be substantially the same obtainable with an adjacent unsaturated carbon-carbon bond such as, for instance, that of a vinyl ester.

The hydrogenation with molecular para-hydrogen of these unsaturated esters of the carboxylate containing molecules of interest has indeed proven to allow a convenient PHIP-based preparation of the corresponding [1-$^{13}$C]-hyperpolarized carboxylate molecules, or of the corresponding carboxylic acids, that can finally be collected in aqueous solutions ready for use in in-vivo MR applications.

The present invention, therefore, generally relates to a process making use of the Para-Hydrogen Induced Polarization technique for the preparation of [1-$^{13}$C]-hyperpolarized carboxylate containing molecules of diagnostic interest that comprises hydrogenating with molecular para-hydrogen an unsaturated alkenyl or alkynyl ester of the concerned carboxylate molecule, used as a suitable hydrogenable substrate precursor of the carboxylate molecule of interest.

More particularly, in one embodiment the invention relates to a PHIP process for the preparation of [1-$^{13}$C]-hyperpolarized carboxylate containing molecules for use in MR diagnostic applications that comprises the steps of:

a) obtaining an unsaturated alkenyl or alkynyl ester of the carboxylate containing molecule of interest and reacting the unsaturated ester with molecular para-hydrogen, to give the corresponding parahydrogenated ester;

b) inducing a polarization transfer from added polarized H to the $^{13}$C signal of the [1-$^{13}$C]-carboxylate carbon atom to give the corresponding [1-$^{13}$C]-hyperpolarized carboxylate ester;

c) removing the hydrogenated ester moiety and collecting an aqueous solution of the [1-$^{13}$C]-hyperpolarized carboxylate containing molecule, or of the corresponding [1-$^{13}$C]-hyperpolarized carboxylic acid.

In a different embodiment, the above process further comprises employing the collected aqueous solution of the [1-$^{13}$C]-hyperpolarized carboxylate molecule of interest for the in vivo or in vitro, ex vivo MR assessment of biological parameters or metabolic profiles of diagnostic interest.

In a further embodiment the invention relates to the use of unsaturated alkenyl or alkynyl esters as suitable hydrogenable substrate precursor for the preparation of [1-$^{13}$C]-hyperpolarized carboxylate containing molecules of diagnostic interest for MR applications by means of the PHIP technique.

In another embodiment, the invention relates to parahydrogenated alkyl or allyl esters according to the invention as intermediate compounds in a PHIP process for preparing [1-$^{13}$C]-hyperpolarized carboxylate containing molecules for use as metabolic markers.

In a still additional embodiment, the invention relates to a method for the in vivo or in vitro (ex vivo) diagnostic visualization of a body organ, region, fluid or tissue or for the MR-based assessment of a biological parameter or a metabolic profile of diagnostic interest in an individual patient that comprises:
  i) collecting an impurity free aqueous solution of the a [1-$^{13}$C]-hyperpolarized carboxylate molecule of interest according to the process of the invention, as above described;
  ii) administering the said aqueous solution to the individual patient, or contacting the said aqueous solution with an ex vivo sample of a body organ, fluid or tissue of the patient;
  iii) exposing the administered patient, or the contacted ex vivo sample to a radiation frequency allowing to excite the hyperpolarized $^{13}$C-carbon atom of the carboxylate molecule; and
  iv) recording the signal intensity generated by the excited nucleus of the administered carboxylate molecule and/or of any suitable metabolite or catabolite thereof, and
  v) obtaining an image of the individual patient body organ, region or tissue, or suitable estimates of the biological parameter or metabolic profile of interest from recorded signals intensity values.

DETAILED DESCRIPTION OF THE INVENTION

Figure 1:
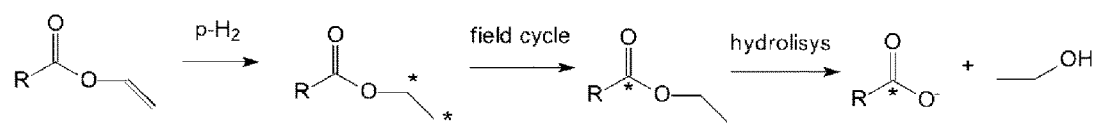
FIG. 1. Schematic presentation of the hyperpolarization procedure according to invention for preparing an aqueous solution of a [1-$^{13}$C]-hyperpolarized carboxylate molecule by means of parahydrogenating: a) a vinyl ester of the carboxylic molecule in an aqueous medium; b) a propargylic ester of the carboxylic molecule in an aqueous medium; c) a propargylic ester of the carboxylic molecule in an organic medium and isolation of the corresponding hyperpolarized carboxylate compound in an aqueous phase.
Figure 1:
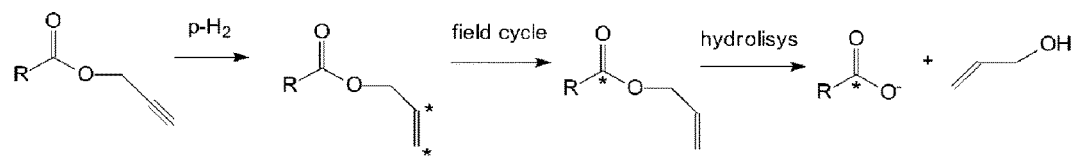
Figure 1:
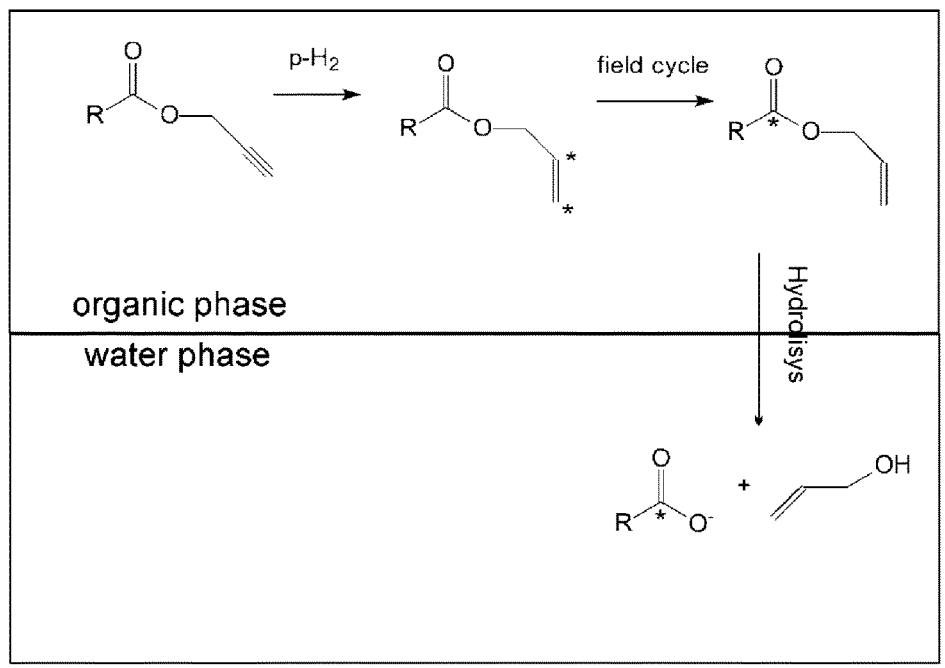

The present invention is directed to unsaturated alkenyl or alkynyl esters and a Para-Hydrogen Induced Polarization process using them as hydrogenable substrate precursor for the preparation of [1-$^{13}$C]-hyperpolarized carboxylate containing molecule of diagnostic interest, especially as MR metabolic probes.

Carboxylate containing molecules according to the invention (whose [1-$^{13}$C]-hyperpolarized derivatives can be conveniently prepared by use of the Para-Hydrogen Induced Polarization process proposed by the present invention) preferably include carboxylic compounds having the following general formula (I)

$$R-C^*(O)-OH \qquad (I)$$

in which
- C* denotes the carboxylate carbon atom undergoing $^{13}C$ hyperpolarization according to the proposed process;
- R is a $C_1$-$C_5$ linear or branched alkyl chain, which is optionally interrupted by, or substituted with, one or more groups selected from carbonyl (—CO—), hydroxyl (—OH), amino (—$NHR_1$), halogen atom(s) and halo-alkyl group(s), or by a carbocyclic aliphatic or aromatic ring, which is, in its turn, optionally substituted by one or more hydroxyl groups;
- $R_1$ is H, or an amino protecting group such as, for instance, trifluoroacetyl, acetyl, benzoyl, carbobenzoxy, tert-butyl carbonate, and, preferably, trifluoroacetyl, and the physiologically acceptable salts thereof.

With $C_1$-$C_5$ linear or branched alkyl chain, or $C_1$-$C_5$ alkyl residue, as used herein, we intend any of the $C_1$-$C_5$ alkyl residue, thus including methyl, ethyl, n-propyl, n-butyl, n-pentyl, isopropyl, isobutyl, sec-butyl, tert-butyl, 2-methylbutyl, where methyl, ethyl, propyl and isopropyl are preferred. With halogens (or halogen atoms, as herein used interchangeably), either alone or as part of a group (e.g. halogeno-alkyl) we refer to chlorine, bromine and fluorine, the latter being preferred.

Halogeno-alkyl groups according to the invention include, for instance perfluorinated $C_1$-$C_3$ alkyl residues, i.e. any $C_1$-$C_3$ alkyl residues wherein all the hydrogen atoms are replaced by fluorine atoms, like, for instance, —$CF_3$, —$C_2F_5$, and —$C_3F_7$ groups, where —$CF_3$ (i.e. trifluoromethyl) is preferred.

Examples of carbocyclic rings according to the invention for instance include either aliphatic or aromatic C6 membered rings such as, preferably, phenyl rings.

Preferably in the above formula (I) R represents a group selected from a $C_1$-$C_5$ alkyl residue of formula —$C_1$-$C_5$, a methylcarbonyl of formula $CH_3C(O)$—, a hydroxyalkyl such as, preferably, the hydroxyethyl residue of formula $CH_3CH(OH)$—, and an aminoalkyl residue of formula $R_2$—$CH(NHR_1)$— in which $R_1$ is as defined above, and $R_2$ is H or $C_1$-$C_4$ linear or branched alkyl chain such as, preferably, methyl, ethyl, propyl, isopropyl, sec-butyl, and iso-butyl, which is optionally substituted by a hydroxy (—OH) group, or a phenyl or hydroxyphenyl ring.

More preferably, R is selected from the group consisting of methyl, propyl, hydroxyethyl, methylcarbonyl and an aminoalkyl residue of formula $R_2$—$CH(NHR_1)$— in which $R_1$ is H and $R_2$ is H or $C_1$-$C_4$ linear or branched alkyl chain as above defined, which is optionally substituted by a hydroxy (—OH) group, or a phenyl or hydroxylphenyl ring, such as, most preferably, isopropyl, iso-butyl, sec-butyl, 1-hydroxyethyl, hydroxylmethyl and p-hydroxybenzyl.

In one preferred embodiment, in the above formula (I) R is a methyl residue (—$CH_3$), and the carboxylate containing molecule of interest according to the invention is the acetate.

In another preferred embodiment, in the above formula (I) R is the hydroxyethyl residue of formula $CH_3CH(OH)$— and the carboxylate containing molecule of interest according to the invention is the lactate.

In a further preferred embodiment, in the above formula (I) R is an amino alkyl group of formula $R_2$—$CH(NHR_1)$— in which $R_1$ is H and $R_2$ is H, or a group selected from isopropyl, iso-butyl, sec-butyl, hydroxymethyl, 1-hydroxyethyl and p-hydroxybenzyl, and the carboxylate containing molecule of interest according to the invention is a natural amino acid.

In an especially preferred embodiment of the invention, in the above formula (I) R is a methylcarbonyl group of formula $CH_3C(O)$— and the carboxylate containing molecule of interest according to the invention is the pyruvate.

Carboxylate containing molecule according to the invention further comprise, as formerly said, the physiologically acceptable salts of the compounds of the above formula (I).

With pharmaceutically acceptable salt, as used herein, we refer to derivatives of the carboxylate compounds of the above formula (I) in which the carboxylic group not yet internally neutralized is in the form of a non-toxic, stable salt which do not destroy or affect the activity of the hyperpolarized compound.

Suitable examples of the said salts typically include alkali or organic salts of the carboxylic acidic residue of formula (I).

To this extent, preferred cations of inorganic bases which can be suitably used to salify the compounds of the invention comprise ions of alkali or alkaline-earth metals such as potassium, sodium, calcium or magnesium. Preferred cations of organic bases comprise, inter alia, those of primary, secondary and tertiary amines such as ethanolamine, diethanolamine, morpholine, glucamine, N-methylglucamine, N,N-dimethylglucamine. Preferred cations of amino acids comprise, for example, those of aspartic and glutamic acids.

Particularly preferred are sodium and potassium salts.

The carboxylate compounds set forth by the above formula (I) do not include a suitable unsaturated carbon-carbon bond in the R residue, thus they cannot be hyperpolarized by suitable addition of molecular para-hydrogen to an existing unsaturation bond and polarization transfer to the $^{13}C$ carbon atom of the carboxylate group.

The solution proposed by the present invention comprises obtaining unsaturated alkenyl or alkynyl esters, and preferably, $C_2$-$C_4$ linear or branched alkenyl or alkynyl esters of the above carboxylate compounds of formula (I) and using the obtained unsaturated esters as convenient hydrogenable substrate precursors of the desired [1-$^{13}C$]-hyperpolarized carboxylate molecules.

Within the scopes of the present invention, the terms "substrate precursor" or "hydrogenable precursor" or "unsaturated precursor" or, simply, "precursor", used herein interchangeably, refer to an unsaturated molecule including one unsaturated bond, e.g. a double or a triple carbon-carbon bond, yielding the desired hyperpolarized product by hydrogenation of the said unsaturated bond with molecular para-hydrogen, transfer of the polarization to a non-proton nucleus, and conversion of the obtained hydrogenated compound in the desired hyperpolarized product.

Example of hyperpolarizable non-proton nucleus (or heteronucleus) typically include a $^{19}F$, $^{13}C$, $^{15}N$ or $^{29}Si$. According to present invention, unless otherwise provided, with the term hyperpolarizable heteronucleus we refer to a $^{13}C$, and, more particularly, we refer to the $^{13}C$-carboxylic carbon atom (or 1-$^{13}C$-carbon atom) of the carboxylate molecule of interest. Substrate precursors for the use of the present invention are unsaturated alkenyl or alkynyl esters of the carboxylate molecule of interest, namely esters that include one unsaturated bond, e.g. a double or a triple carbon-carbon bond in the hydrocarbon R' chain of the —O—R' ester moiety, and are easily hydrogenable.

An object of the present invention thus relates to the use of an unsaturated alkenyl or alkynyl ester of a carboxylate containing molecule of diagnostic interest as hydrogenable substrate precursor for the preparation of the corresponding [1-$^{13}C$]-hyperpolarized carboxylate containing molecule by use of the PHIP technique.

More particularly, the present invention relates to a PHIP process for the preparation of [1-$^{13}C$]-hyperpolarized carboxylate containing molecules of diagnostic interest which comprises hydrogenating with molecular para-hydrogen unsaturated alkenyl or alkynyl ester of the concerned carboxylate molecule.

To this extent, unsaturated alkenyl or alkynyl esters according to the invention, namely for use as hydrogenable substrate precursor for the preparation of [1-$^{13}$C]-hyperpolarized carboxylate compound with the PHIP technique, preferably include $C_2$-$C_4$ linear or branched alkenyl or alkynyl esters of the carboxylate containing molecule of interest that, more preferably, are selected from vinyl, allyl or propargyl esters of the said concerned carboxylate molecule.

According to a preferred embodiment, the unsaturated esters according to the invention are $^{13}$C enriched, or $^{13}$C labeled, as herein used interchangeably. The term "enriched" or, alternatively "labeled" means that the concentration of the non-zero spin nucleus in the compound is above the typical value of natural abundance of said nuclei, preferably above at least 10% of natural abundance, more preferably above at least 25%, and even more preferably above at least 75% of its natural abundance and most preferably above at least 90% of its natural abundance. According to the present invention, the enrichment is concentrated on the carboxylic 1-C carbon atom of the ester that becomes $^{13}$C-enriched (or [1-$^{13}$C]-enriched, as herein used interchangeably). Said non-zero $^{13}$C nucleus confers to the obtained carboxylate containing molecule (or carboxylate product, or, simply, product, as used herein interchangeably) a T1 relaxation time of at least 5 seconds (indicated with s), preferably of at least 10 s, preferably of at least 20 s, preferably of at least 30 s, and even more preferably of at least 40 s, measured in a solution subjected to a magnetic fields of from about 0.5 mT to about 20 T (Tesla). The appropriate $^{13}$C enrichment may be natural, when the carboxylate ester is naturally 1-$^{13}$C enriched, or it may include the selective enrichment (or $^{13}$C labeling, as herein used alternatively) of the carboxylic 1-C carbon atom of the molecule. To this extent, commercially available enriched precursors can be suitably employed or, in case, the enrichment of choice can be achieved by chemical synthesis, or biological labeling, according to well-known prior art teachings.

Unsaturated esters for the use of the instant invention as substrate precursor should be highly polarisable. In particular, preferred esters are polarisable to a degree corresponding to at least 5%, preferably at least 10% and, more preferably of at least 20% or even higher, and are capable to maintain a $^{13}$C net magnetization in the carboxylate product within the above limits after removal of the hydrogenated moiety and isolation of the free hyperopolarized carboxylate molecule of diagnostic interest.

To this extent, after hydrogenation with molecular para-hydrogen and transfer of the polarization to the carboxylic $^{13}$C-carbon atom, preferred unsaturated ester according to the invention should allow the easy removal of the hydrogenated moiety in an aqueous medium, typically by hydrolysis, thus enabling a quick isolation of an aqueous solution of the free [1-$^{13}$C]-hyperpolarized carboxylate molecule, ready for use in in vivo MR applications.

In general terms, the unsaturated esters for the use of the invention can be, preferably, represented by the following general formula (II)

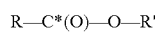   (II)

in which:

C* denotes the naturally $^{13}$C enriched or, optionally, $^{13}$C labeled carboxylate carbon atom undergoing $^{13}$C hyperpolarization, R is as above defined for the formula (I), and R' is a $C_2$-$C_4$ linear or branched hydrocarbon chain comprising a double or triple carbon-carbon bond.

Preferably, in the above formula (II) R' is an alkenyl or alkynyl residue selected from vinyl (of formula —CH=CH$_2$), allyl (of formula —CH$_2$—CH=CH$_2$) and propargyl (of formula —CH$_2$—C≡CH).

More preferably, R' is a vinyl or a propargyl residue.

In one preferred embodiment, the invention refers to unsaturated esters of the above formula (II) in which R' is a vinyl residue.

In another preferred embodiment, the invention refers to unsaturated esters of formula (II) in which R' is a propargyl residue.

An additional object of the invention relates to a process that comprises hydrogenating with molecular para-hydrogen an unsaturated alkenyl or alkynyl ester, preferably having the above formula (II), for preparing [1-$^{13}$C]-hyperpolarized carboxylate containing molecules of diagnostic interest, especially as MR metabolic probes, by use of the Para-Hydrogen Induced Polarization technique.

More particularly, in one preferred embodiment the invention relates to a process for the preparation of [1-$^{13}$C]-hyperpolarized carboxylate containing molecules of formula (I) that comprises the steps of:

a) obtaining an unsaturated alkenyl or alkynyl ester of the carboxylate containing molecule of interest and reacting the unsaturated ester with molecular para-hydrogen, to give the corresponding parahydrogenated ester;

b) inducing a polarization transfer from added para-hydrogen to the $^{13}$C signal of the [1-$^{13}$C]-carboxylate carbon atom to give the corresponding [1-$^{13}$C]-hyperpolarized ester;

c) removing the hydrogenated ester moiety and collecting an aqueous solution of the [1-$^{13}$C]-hyperpolarized carboxylate containing molecule, or of the corresponding [1-$^{13}$C]-hyperpolarized carboxylic acid.

Preferably, the unsaturated ester obtained at the step a) of the process is an alkenyl or alkynyl ester of the above formula (II).

To this extent, suitable unsaturated esters of the above formula (II) can be commercially available, as is the case, for instance, of the vinyl acetate, or may be conveniently obtained by using conventional preparation procedures, easily available to those skilled in synthetic organic chemistry techniques. The preparation of non-limiting examples of representative unsaturated esters according to the invention is moreover provided in the experimental section which follows.

The hydrogenation of the unsaturated ester according to the step a) of the process of the invention is performed by use of a PHIP technique, in the presence of a suitable hydrogenation catalyst. Typically, the latter is used in catalytic amounts known to a skilled person, for instance in a substrate/catalyst ratio ranging from 10:1 to 5:1.

A further embodiment of the invention therefore relates to parahydrogenated alkyl or allyl esters, e.g. obtained by hydrogenating with molecular para-hydrogen unsaturated esters according to the invention, preferably of the above formula (II), finding application as intermediate compounds in a PHIP process for preparing hyperpolarized molecules, e.g. for preparing [1-$^{13}$C]-hyperpolarized carboxylate containing molecules for use as MR metabolic markers.

More particularly, in a further embodiment the present invention relates to a para-hydrogenated ester of formula (III)

$$R—C^*(O)—O—R''  \quad (III)$$

in which C* and R are as above defined, and R" is a parahydrogenated alkyl or allyl residue such as, preferably, a parahydrogenated ethyl, propyl or allyl and, most preferably, ethyl or allyl, e.g. obtained by hydrogenation with molecular para-hydrogen of an unsaturated ester of the above formula (II) in which R' represents, respectively, a vinyl, an allyl or a propargyl and, most preferably, a vinyl or a propargyl residue, as well as the use thereof in a PHIP process, e.g. as intermediate compound for the preparation of [1-$^{13}$C]-hyperpolarized carboxylate containing molecules.

In an additional embodiment the invention relates to a process for the preparation of hyperpolarized molecules by use of the Para Hydrogen Induced Polarization technique that comprises obtaining a para-hydrogenated ester of formula (III) as an intermediate compound.

Figure 2:
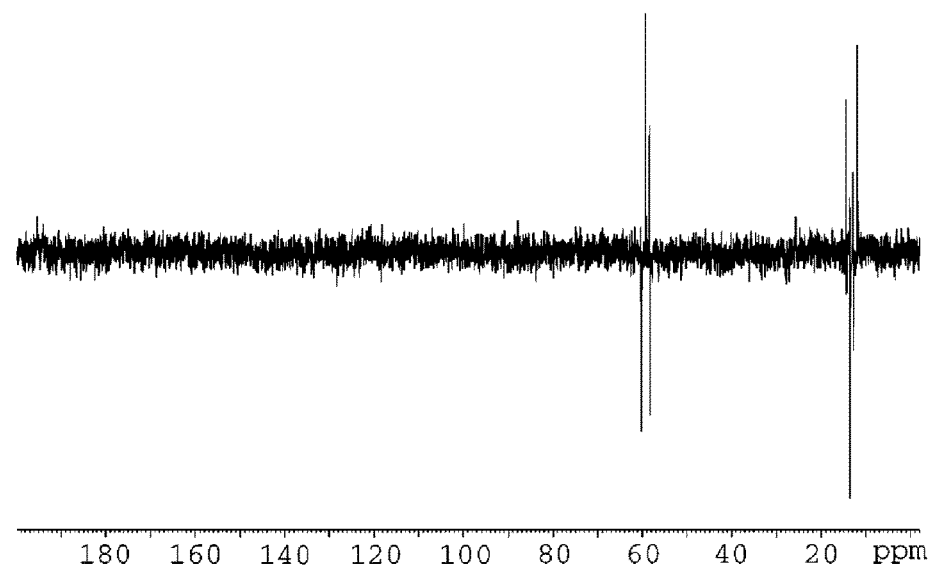
FIG. 2. $^{13}$C-NMR spectra (14 T, 298 K, D$_2$O) of ethyl acetate after parahydrogenation in water of the vinyl ester showing that, before application of the field cycling, the only detectable 13C signals are those of the aliphatic carbon atoms of the ethyl group that are affected by the parahydrogen atoms linked thereto, whereas the carbonyl signal is unaffected and, hence, non-polarized.
Figure 10:
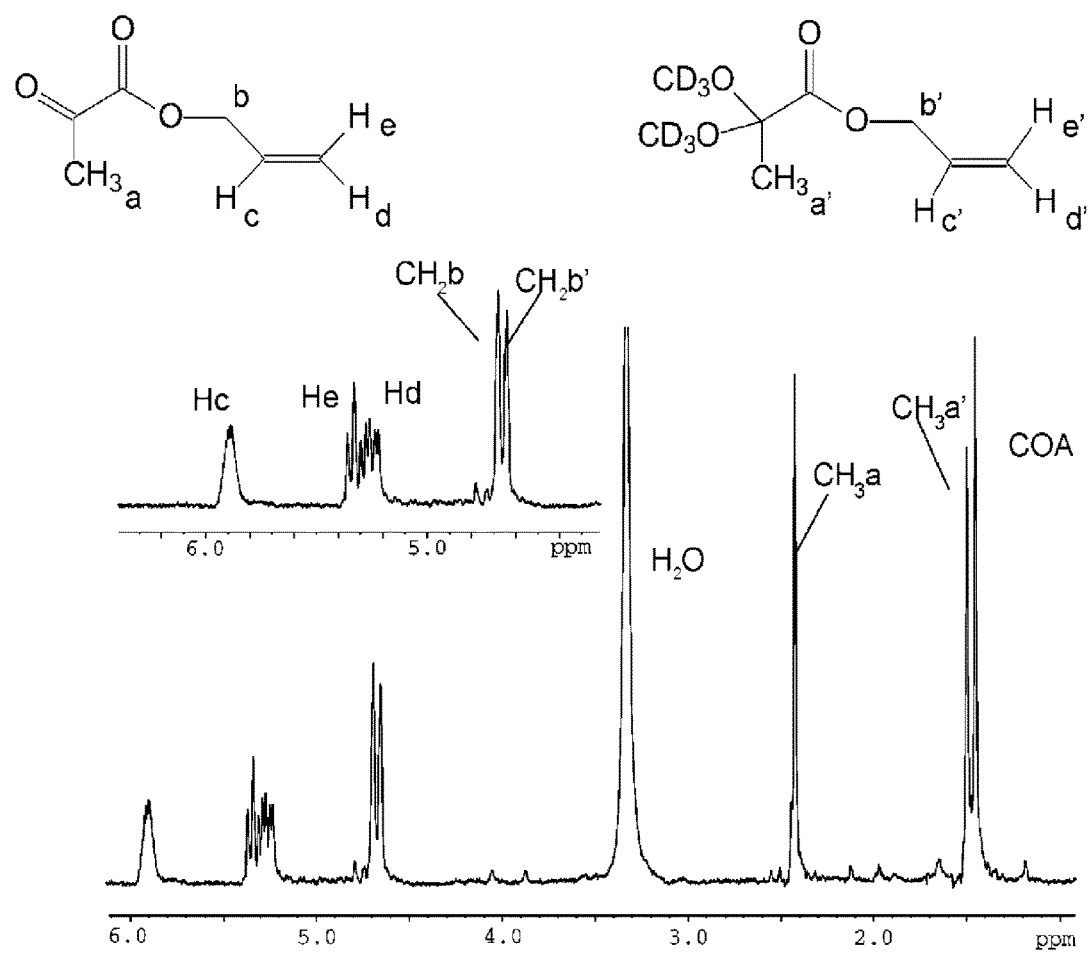
FIG. 10. 1H NMR spectrum of hydrogenation product allyl-pyruvate: c, c' 5.75 ppm (m); e, e' 5.15 ppm (dd, $^2$J=17.5 Hz, 3J=17 Hz); d,d' 5.07 ppm (dd, $^2$J=17.5 Hz, $^3$J=10 Hz); b 4.49 ppm (d $^3$J=5.93 Hz); b' 5.54 ppm (d, $^3$J=5.5 Hz); a 2.27 ppm (s); a' 1.28 ppm (s); COA cyclooctane derived from the hydrogenation catalyst).
Figure 11:
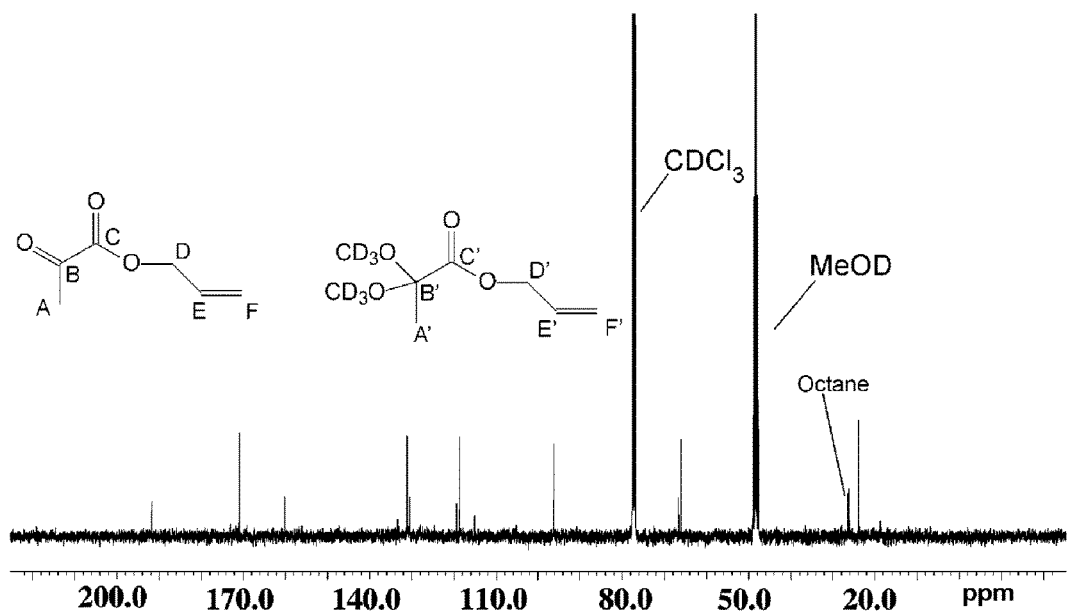
FIG. 11. 13C spectrum of the hydrogenation product allyl-pyruvate in the hydrogenation solvent MeOD/CDCl3. A: 26 ppm; A' 24 ppm; D: 66.5 ppm; D' 66 ppm; B' 96 ppm; E,F 119, 131 ppm; E', F' 132, 118 ppm; C 160 ppm; C' 171 ppm; B 192 ppm; the observed Octane signal is from the hydrogenation catalyst in the organic solution.

Suitable examples of the para-hydrogenated intermediates of formula (III) according to the invention for instance include the ethyl acetate obtained by addition of molecular para-hydrogen to a the vinyl acetate precursor, which 13C-NMR characterization is provided in FIG. 2, the allyl pyruvate obtained by addition of molecular para-hydrogen to a propargyl-pyruvate precursor, which 1H-NMR characterization is provided in FIG. 10, while the 13C spectrum is provided in FIG. 11.

According to the process of the present invention, the hydrogenation of the unsaturated ester with molecular para-hydrogen can conveniently be carried out either in an aqueous medium, or in an organic solvent, or suitable mixtures of organic solvents.

In one embodiment of the invention, the steps a) of the process including reacting the unsaturated ester with molecular para-hydrogen is carried out in an aqueous solvent and in the presence of a water soluble hydrogenation catalyst, according to hydrogenation procedures known in the art.

To this extent, with the expression "aqueous solvent" or "aqueous medium", as used herein interchangeably, we refer to water and, preferably, to sterile water, which can optionally be properly buffered, for instance at an around neutral pH value, for instance comprised from 6 to 8, and, preferably, of about 7, by use of appropriate buffers, such as, for instance, phosphate buffer ($H_3PO_4/H_2PO_4$).

Examples of catalysts suitable for the use in aqueous solvents include rhodium(I) complexes of formula [Rh (diphosphine)diene)]$^+$[anion]$^-$, where the diphosphine is a chelating phosphine preferably selected from (1,4-Bis ($R_1R_2$)ethane), (1,4-Bis($R_1R_2$)butane), where $R_1$ and $R_2$, equal or different the each other, comprise sulfonated groups such as, for instance, DPPETS (1,2-bis[bis(m-sodiosulphonatophenyl)phosphino]ethane)(1,2-Bis(diphenylphosphino) ethane), DPPBTS (tetrasulfonated 1,4-bis(diphenylphosphino)butane, in which $R_1=R_2$), DAPBTS (tetrasulfonated bis(dianisylphpsphino)butane), chiral sulfonated diphosphines such as, for instance, sulfonated CHIRAPHOS (2,3-bis[bis(m-sodiosulphonatophenyl)phosphino]butane), and sulfonated BINAP (2,2-bis[bis(m-sodiosulphonatophenyl) phosphino]-1,1-binaftile). The diene is preferably selected from 1,5-cyclooctadiene and norbornadiene, and the anion can be any anion, but, preferably, tetrafluoroborate or trifluoromethyl solfonate.

Preferred are hydrogenation catalysts in which the phosphine group is diphenylphosphinobutane, and the [Rh(NBD) phos][BF$_4$] (where NBD is norbornadiene, and phos is 1,4-bis[(phenyl-3-propane sulfonate)phosphine]butane disodium salt) is particularly preferred.

According to one practical implementation, the hydrogenation reaction of the unsaturated substrate according to the invention is suitably carried out by use of a hyperpolarizer where hydrogen is introduced at high pressure, typically higher than 6 and preferably of at least 8 bar, into a reactor chamber causing the nebulization of the solution containing the substrate and the catalyst, and which allows to optimize the hydrogen solubility. The hydrogenation reaction is preferably carried out at a temperature comprised from 30° C. to 90° C. and, more preferably, from 60° C. to 90° C.

It is clear to those skilled in the art that when the hydrogenation reaction is carried out in an aqueous medium, as above disclosed, either the hydrogenation catalyst and the unsaturated substrate molecule should be soluble in this medium.

To this extent, a little amount of a short-chain alcohol, such as, for instance, methanol or ethanol or, alternatively of any water soluble organic solvent such as, preferably, acetone, can be added to the aqueous medium, in an amount at least higher than 10%, preferably ranging from 10% to 30% and, more preferably, from 10% to 20% of the total solvent amount, consenting to increase both the catalyst efficacy and the substrate and hydrogen gas solubility in the aqueous medium.

Alternatively, a short-chain alcohol such as, preferably, methanol or ethanol and, more preferably, methanol, can be suitably used as hydrogenation reaction solvent. In this case, preferred hydrogenation catalyst is [Rh(COD)dppb][BF$_4$], where COD is cyclo-1,5-octadiene and dppb is 1,4-bis (diphenylphosphino)butane).

Upon hydrogenation of the unsaturated ester with para-hydrogen, the polarization is transferred from the added polarized H to the $^{13}$C signal of the [1-$^{13}$C]-carboxylate carbon atom via scalar coupling (or nuclear Overhauser effect) by use of the know means.

To this extent, in order to profitably use a parahydrogenated compound as an effective $^{13}$C MRI contrast agent, it is necessary that the "anti-phase" signal of the hyperpolarized carbon atom, obtained through polarization transfer from the added parahydrogen, is totally converted in an "in-phase" signal, useful for imaging acquisition. This step can be performed by using an appropriate pulse sequence as taught, for instance, by Goldman M. et al, in the above cited reference (C. R. Phisique 2005, 6, 575), or by applying an appropriate field cycling procedure to the parahydrogenated product. This last includes rapidly introducing (non-adiabatically) the hydrogenated sample into a magnetic screen (field intensity=0.1 µT), and then slowly removing (adiabatically) the screen to bring the sample to field values corresponding to the Earth's magnetic field (50 µT) (in this respect see, for instance, C. R. Phisique 2004, 5, 315).

According to a preferred embodiment, the step b) of the process of the invention is carried out by application of an appropriate field cycling procedure to the para-hydrogenated ester obtained at the step a) of the process, consenting to promote the polarization transfer from the proton nuclei (deriving from the parahydrogen addition to the unsaturated ester) to the non-proton nucleus of interest, namely the [1-$^{13}$C]-carbon atom of the carboxylate molecule to give the corresponding [1-$^{13}$C]-hyperpolarized carboxylate molecule.

It is worth nothing that, in general terms, the polarization transfer from para-hydrogen to the heteronucleous of interest is mainly driven by scalar coupling (or j coupling), and a heteroatom adjacent to the unsaturation typically acts as recipient of the polarization transfer from the scalarly coupled para-hydrogen protons (as shown, for instance, in FIG. 2). To this extent, the intensity of the heteronuclear polarization depends on all the j couplings involved in the spin systems formed. Thus, for instance, for $^{13}C$ compounds, it has been calculated (Barkemeyer J.; Haake, M.; Bargon J. J. Am. Chem. Soc. 1995, 117, 2927-2928) that the maximum polarization transfer from parahydrogen protons (indicated with A and A') to an heteroatom (indicated with X) forming an AA'X spin system with parahydrogen protons can be reached when the J couplings among all the nuclei stay into a defined ratio. In particular, being $J_{AX}-J_{A'X}$ the difference between scalar coupling of the two protons and the heteroatom and $J_{AA'}$ the scalar coupling between the two protons on the product, the polarization transfer is maximum when the value of the ratio $|J_{AX}-J_{A'X}|/J_{AA'}$ is $\sqrt{8}$. As the JAA' constants is into a range from 5 to 15 Hz, then the optimal difference between the heteronucelar J coupling (proton-carbon coupling) is in the range 15-45 Hz. Such high scalar coupling values can be achieved when the two parahydrogen protons are added at a distance of two or three (bonds) from the heteroatom to which the polarization is transferred, and gradually decreases with increasing distance from the added parahydrogen protons.

From all the foregoing, a skilled person in the art would have never expected that one could observe a satisfactory heteronuclear polarization, useful for MR diagnostic applications and metabolic MR assessments, by polarization transfer from parahydrogen protons placed at a distance of more than two or three bonds from the $^{13}C$ carbon atom of interest. Even less one would have expected to could observe a heteronuclear $^{13}C$ polarization substantially equivalent or comparable to that obtained with a heteronucleus placed at the (above identified) optimal distance with $^{13}C$ carbon atoms rather placed at a distance of 4-5 bonds from the added para-hydrogen protons.

Figure 3:
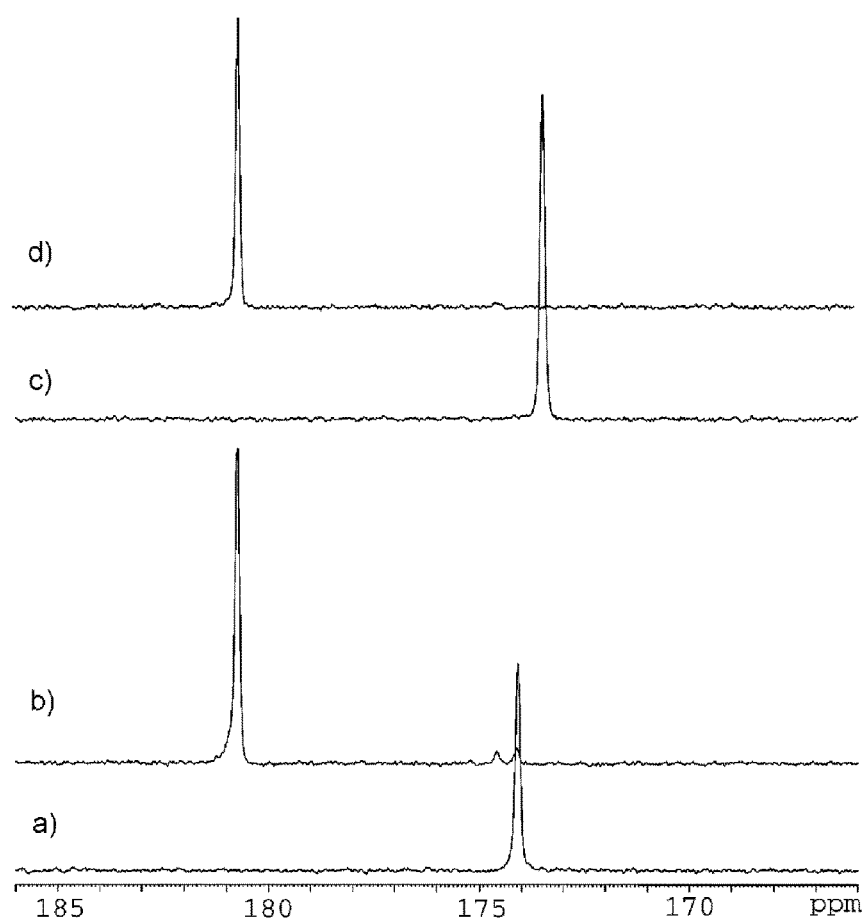
FIG. 3. $^{13}$C-NMR spectra (14 T, 298 K, D$_2$O) a) $^{13}$C hyperpolarized signal of the ethyl acetate after para-hydrogenation in water of the vinyl-ester and field cycling; b) sodium acetate obtained from hydrolysis of hyperpolarized ethyl acetate in water; c) allyl-acetate from parahydrogenation of propargyl-acetate in water and field cycling; d) Na-acetate from hydrolysis of allyl-acetate.

Instead, we have unexpectedly observed that, after application of magnetic field cycle, a substantially identical hyperpolarization of the 13C signal of the [1-$^{13}C$]-carboxylate carbon atom can be achieved by polarization transfer from both the polarized H proton nuclei of the parahydrogenated vinyl ester (having the recommended 3 bond distance to the involved 13C heteronucleous) and the polarized H proton nuclei of the corresponding parahydrogenated propargyl ester, having an increased (4-5 bonds) distance to the heteronucleous of interest, as shown, for instance, in FIG. 3, comparing the intensity of the carboxylic 13C signals signal obtained from parahydrogenated vinyl and propargyl esters after application of the field cycling.

On the contrary, as shown in FIG. 2, in the absence of an induced polarization transfer, (i.e. before application of the field cycling), the only detectable 13C signals are those of the aliphatic adjacent carbon atoms of the ethyl group that are linked to, and, hence, affected by, the para-hydrogen atoms added to the vinyl residue, while no detectable signal is observed for the carboxylic 13C carbon atom, placed at a greater distance and, thus, substantially unaffected.

These unexpected results make it possible to prepare esters suitably hyperpolarized to the carboxylic [1-$^{13}C$]-carbon atom and, in turn, to obtain suitably [1-$^{13}C$]-hyperpolarized carboxylate containing molecules of diagnostic interest from unsaturated allyl or propargyl precursor thereof, thereby allowing to obtain [1-$^{13}C$]-hyperpolarized carboxylate compounds endowed with a satisfactory degree of polarization by use of the PHIP technique even in the absence of a direct unsaturated precursor thereof, as well as of an appropriate vinyl ester.

Rightly after its preparation, the [1-$^{13}C$]-hyperpolarized ester for instance obtained at the step b) of the process of the invention is quantitatively converted into the desired [1-$^{13}C$]-hyperpolarized carboxylate compound, or in the corresponding [1-$^{13}C$]-hyperpolarized carboxylic acid, that is then collected in an aqueous solution ready for use in in vivo applications. According to a preferred embodiment of the invention, the said quantitative conversion is performed by hydrolytic removal of the hydrogenated ester moiety, yielding the free carboxylate of interest, or the corresponding carboxylic acid.

To this extent, the expression "quantitative conversion" is herein used to indicate a chemical transformation (preferably a hydrolysis) in the amount of 20% or more, preferably 50% or more, more preferably 75% or more and even more preferably of at least 90%, particularly preferred being a transformation of at least 95% of the ester precursor into the corresponding free carboxylate.

The term "hydrolysis", as used herein, refers to a chemical reaction in which the water reacts with a starting compound to produce one or more resulting compound(s); it typically involves the splitting of a bond (the ester bond) on the starting compound and the optional addition of a hydrogen cation and/or of a hydroxide anion to the structure of the starting compound, to obtain the resulting compound(s). Generally speaking, the hydrolysis reaction can be carried out under acidic (pH<7), basic (pH>7) or even neutral conditions (pH=7), whereas basic conditions, for instance corresponding to a pH solution preferably comprised from 7 to 14, more preferably form 8 to 14 and, most preferably, from 10 to 14 are to be considered as particularly preferred for the process of the present invention, as will be described herein below in more details.

In line with all the above, the step c) of the process of the invention comprises hydrolyzing the [1-$^{13}C$]-hyperpolarized ester obtained at the step b) of the process to the corresponding water soluble [1-$^{13}C$]-hyperpolarized carboxylate containing compound, that is then collected in an aqueous solution.

More particularly, according to one preferred implementation, the step c) of the process of the process of the invention is carried out by adding the [1-$^{13}C$]-hyperpolarized ester obtained at the step b) of the process in an aqueous solution with a suitable amount of a base, e.g. NaOH, or NaHCO$_3$, or Na$_2$CO$_3$, as well as organic or inorganic compounds having basic aqueous reaction (e.g. trimethylol aminomethane, also known as tromethamine, or trisodium phosphate) for instance as schematized in schemes a) and b) of FIG. 1.

Particularly preferred for the scope of the instant invention is the use of aqueous NaOH.

For instance, an aqueous solution of the hyperpolarized ester obtained at the step b) of the process with a 10-100 mM concentration is hydrolyzed in the presence of NaOH 0.1-1 M, that is added to the aqueous solution at a temperature ranging from about 20° to 100° C., preferably from 40° to 80° C. and most preferably from 60° to 80°, thereby leading to an aqueous solution of the [1-$^{13}C$]-hyperpolarized carboxylate compound.

To this extent, it must be considered that, for in vivo MR applications, the biocompatibility of the obtained aqueous solutions of hyperpolarized products is required. Therefore, after steps a) to c), the above process according to the invention comprising carrying out the $^{13}C$ polarization of the precursor ester molecule in an aqueous medium as above described preferably includes an additional step d) comprising removing hydrogenation catalyst and optional organic co-solvent(s) from the aqueous solution of the $[1-^{13}C]$-hyperpolarized carboxylate compound obtained at step c), thereby obtaining an aqueous solution of $[1-^{13}C]$-hyperpolarized carboxylate containing molecule of interest suitable for use in in vivo applications.

This last task can, for instance, be achieved by quick evaporation of the aqueous solution of the hyperpolarized product, for instance by spraying the solution into a chamber or flask connected to a vacuum pump. The removal of the potentially toxic Rh(I) complex may then be conveniently performed, e.g. by elution of the aqueous solution (of the hyperpolarized molecule) resulting from removal of any optional organic solvent or co-solvent on a micro-column containing less than 1 ml of a cationic exchange resin, retaining the positively charged hydrogenation catalyst.

To overcome all the above purification steps, according to a particularly preferred embodiment, the steps a) of the process of the invention, including reacting the unsaturated ester with molecular para-hydrogen, is carried out in an organic solvent, or a suitable mixture of organic solvents, and in the presence of a hydrogenation catalyst soluble in an organic medium and insoluble in an aqueous solvent.

Organic solvents suitable for the purpose of the invention are immiscible with water and, preferably, comprise organochlorinated solvents such as, for example, chloroform, dichloromethane, carbon tetrachloride, ethers such as, for instance, diethylether, diisopropylether and butylether and aliphatic hydrocarbons such as, for instance, pentane, hexane, heptane, octane and cyclohexane, ethyl acetate and so on.

Among them, preferred are chlorinated solvents, wherein particularly preferred are chloroform and dichloromethane as well as suitable mixtures thereof or, optionally, mixtures of the above solvents with a minimum amount of a short-chain alcohol such as, typically, ethanol or, preferably, methanol, or, alternatively of acetone. To this extent, with minimum amount as used herein we intend an amount which is less than 30%, preferably ranging from 10% to 30%, and, more preferably, from 10 to 20% of the total solvent amount, leading to undetectable residues in the aqueous solutions of the hyperpolarized carboxylate containing molecules finally recovered. Optional traces, e.g. obtained by using higher amounts of water-miscible solvents, can on the other side, be suitably removed from collected aqueous solution of the desire hyperpolarized molecule, for instance by its rapid evaporation or spry-drying, as formerly discussed.

Examples of catalysts suitable for the use of the present invention include rhodium complexes of formula [Rh(diphosphine)diene)]$^+$[anion]$^-$, where the diphosphine is preferably selected from DPPB (1,4-Bis(diphenylphosphino)butane), DPPE (1,2-Bis(diphenylphosphino)ethane) and derivatives thereof including, for instance, the chiral phosphines such as DINAP (2,2'-Bis(diphenylphosphino)-1,1'-binaftyl), CHIRAPHOS (2,3-diphenylphosphinobutane), DIOP (1,4-Bis(diphenylphosphino)-1,4-bisdeoxy-2,3-O-isopropyliden-L-treitol), and DIPAMP (1,2-Bis[(2-methoxyphenyl)(phenilphosphino)]ethane); the diene is preferably selected from 1,5-cyclooctadiene and norbornadiene, and the anion can be any anion, but, preferably, tetrafluoroborate or trifluoromethyl solfonate.

Among them, preferred are catalysts in which the phosphine group is diphenylphosphinobutane, while the [Bis(diphenylphosphinobutane)(1,5-cyclooctadiene)]Rh(I) is particularly preferred.

In practical terms, the hydrogenation of the unsaturated substrate is, for instance, carried out by spraying the organic solution comprising the substrate and the catalyst into a reaction chamber previously pressurized with para-$H_2$ at a pressure preferably comprised from 6 to 10, more preferably from 8 to 10 and most preferably with about 10 atm of para-hydrogen. The hydrogenation reaction is preferably carried out at a temperature comprised from 40° to 90° C. and, more preferably, from 70° to 90°.

Right upon hydrogenating of the unsaturated ester with para-hydrogen, the polarization is transferred from the added polarized H to the $^{13}C$ signal of the $[1-^{13}C]$-carboxylate carbon atom.

To this extent, according to a preferred implementation, the polarization transfer according to step b) of the process of the invention is carried out by application of an appropriate field cycling procedure to the parahydrogenated ester, for instance obtained at the step a) of the process, as above discussed, promoting the desired polarization transfer from added proton nuclei to the $[1-^{13}C]$-carbon atom of the carboxylate molecule (i.e. the hydrogenated ester) thus giving an organic solution of the corresponding $[1-^{13}C]$-hyperpolarized ester.

The hydrolytic removal of the hydrogenated ester moiety is then carried out according to the step c) of the proposed process, yielding the desired water soluble $[1-^{13}C]$-hyperpolarized carboxylate compound, or the corresponding $[1-^{13}C]$-hyperpolarized carboxylic acid, that is then collected as an aqueous solution, ready for use in in vivo applications.

According to a preferred embodiment, the step c) of the process of the invention is carried out by simply diluting the organic solution of the hyperpolarized ester preferably obtained, as said, at the step b) of the process with an appropriate aqueous solution promoting the hydrolysis of the $[1-^{13}C]$-hyperpolarized ester to the corresponding water soluble $[1-^{13}C]$-hyperpolarized carboxylate compound, or corresponding carboxylic acid, for instance as schematically shown in FIG. 1, scheme c).

It stems from the foregoing that, according to a particularly preferred embodiment, the process of the invention comprises obtaining an insoluble or scarcely water soluble $[1-^{13}C]$-hyperpolarized ester in an organic medium, e.g. from an unsaturated ester of formula (II) soluble in an organic solvent but insoluble or scarcely water soluble, for instance as above described; quantitatively converting it into the corresponding water soluble $[1-^{13}C]$-hyperpolarized carboxylate compound by hydrolytic removal of the hydrogenated ester moiety carried out by dilution of the organic solution (of the hyperpolarized ester) with a suitable aqueous solution, and then collecting the obtained $[1-^{13}C]$-hyperpolarized carboxylate compound in the aqueous phase, by phase transfer extraction, as an impurity-free aqueous solution ready for use in in vivo application.

According to the present invention, and unless otherwise indicated, the expressions "poorly water soluble" or "scarcely water soluble", used herein interchangeably with reference to an unsaturated ester of formula (II) or a $[1-^{13}C]$-hyperpolarized ester according to the invention, refer to a compound that has a minimal solubility in water, preferably less than 20%, more preferably, less than 5% and, even most preferably, less than 1% of the total compound amount.

On the other side, and unless otherwise indicated, the terms "aqueous solution" or "suitable aqueous solution" or "appropriate aqueous solution", herein used interchangeably, refer to a sterile water or saline solution, optionally properly buffered, in any case physiologically tolerable and suitable for use in in vivo diagnostic applications, or, moreover, an aqueous solution as defined above, further including a suitable amount of a properly selected reagent capable of promoting the rapid and selective conversion of the hydrogenated ester into the corresponding, water soluble, [1-$^{13}$C]-hyperpolarized carboxylate compound and to generate, as a result, a physiologically acceptable aqueous solution of the same, suitable for use as such in in vivo diagnostic applications, without requiring further purification. Suitable examples of aqueous solution according to the instant invention capable of promoting the hydrolysis of the parahydrogenated substrate to the corresponding carboxylate compound comprise a minimum amount of a base, e.g. NaOH or NaHCO$_3$, or Na$_2$CO$_3$, as well as organic or inorganic compounds with basic aqueous reaction (e.g. trimethylol aminomethane, also known as tromethamine, or trisodium phosphate) or the corresponding deuterated molecules. Particularly preferred for the scope of the instant invention are water solutions of NaOH or of the corresponding deuterated molecule.

However, it is clear from all the foregoing that, when the reagent used for promoting the ester hydrolysis according to the step c) of the process of the invention is not itself physiologically acceptable, such as the case of the NaOH, its quantity in the added aqueous solution must be precisely determined, based on the stoichiometry of the reaction itself, so as to be completely used in the conversion reaction of the parahydrogenated ester to the water soluble and physiologically compatible (at physiological pH condition) free carboxylate, or the exceeding amount has to be suitably neutralized (for instance by addition of a suitable amount of an acid generating with the base a physiologically acceptable salt) so as to result in a physiologically acceptable aqueous solution of the desired carboxylate compound, which is ready for use as such in in vivo applications, without requiring any further purification and/or subsequent formulation.

An aqueous solution of the [1-$^{13}$C]-hyperpolarized carboxylate containing molecule (or carboxylic acid) is, thus, directly collected from step c) of the above preferred process according to the invention, which is impurity-free and usable as such in the in vivo MRI diagnostic imaging, without need of further purification.

Figure 7:
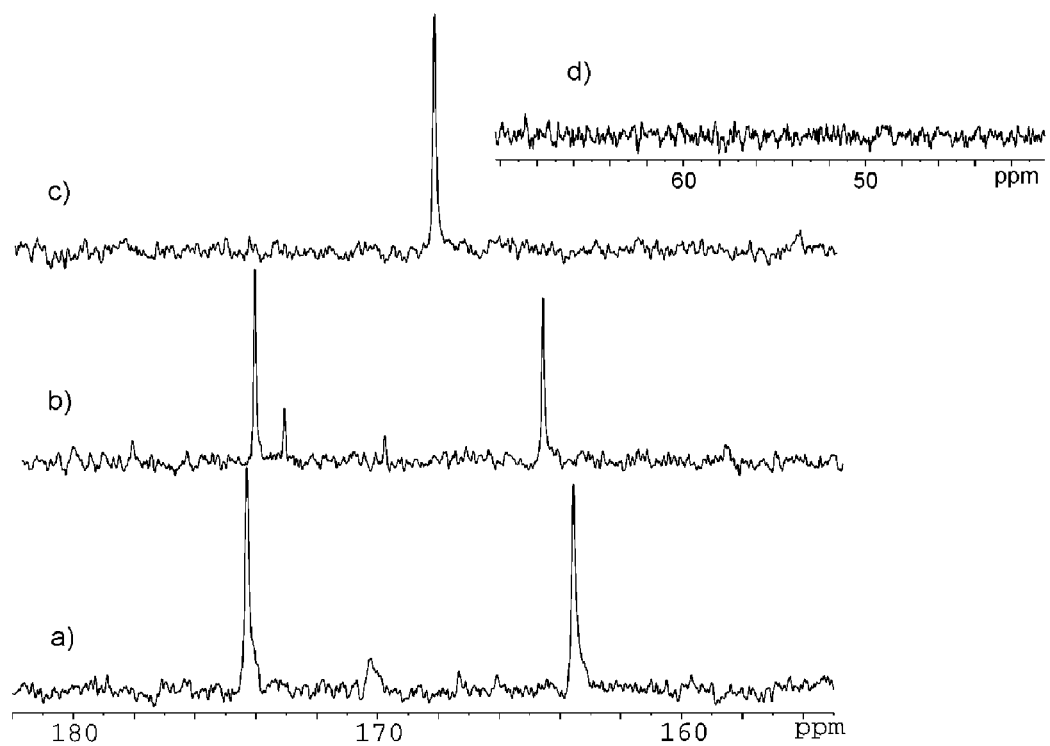
FIG. 7. a) $^{13}$C polarized signal of hydrogenated propargyl-pyruvate (i.e. allyl-pyruvate) obtained in Methanol/CDCl3: allyl-pyruvate carbonylic form (163.8 ppm) and hydrate form (174.2 ppm) ; b) after basic hydrolysis (NaOD 1M) and acidification with DCl (1M) pH=2: pyruvic acid, carbonilic form (164.5 ppm), hydrate form (174 ppm) and emi-acetalic form (173 ppm); c) after basic hydrolysis with NaOD and addition acidification with DCl pH=4: sodium pyruvate (168 ppm); d) the spectrum recorded in the MeOH relevant region, confirming the absence of any detectable MeOH signal.
Figure 9:
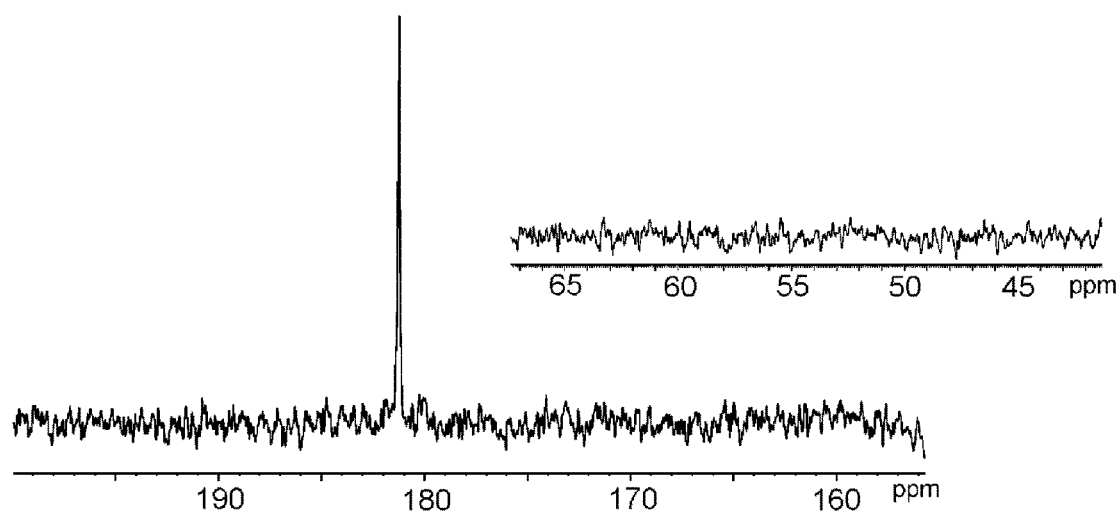
FIG. 9. $^{13}$C-NMR spectra of the aqueous solution directly collected from test of Example 5 showing the $^{13}$C polarized signal (181 ppm) obtained by basic hydrolysis of the $^{13}$C hyperpolarized TFA-allyl glycine, attributed to free glycine. Methanol signal (49.5 ppm) is not observed.

In this respect, no detectable traces of impurities or organic solvents have been observed in the aqueous solutions of [1-$^{13}$C]-hyperpolarized carboxylate containing molecules collected after hydrolysis from experimental tests in which the hyperpolarized ester in obtained in an organic solvent, though comprising methanol or acetone as organic co-solvent. Indeed, no residues of these co-solvents, at least at detectable levels, are found in aqueous solutions obtained from tests of Example 3 (see FIG. 7c) and Example 5 (see FIG. 9) using MeOH as hydrogenation co-solvent.

Hence, according to an especially preferred embodiment the instant invention relates to a Para-Hydrogen Induced Polarization process for the preparation of [1-$^{13}$C]-hyperpolarized carboxylate containing molecules of diagnostic interest that comprises:

a) obtaining a suitable unsaturated alkenyl or alkynyl ester of the optionally [1-$^{13}$C]-enriched carboxylate containing molecule of interest in an organic solvent (or solvent mixture) immiscible with water, which can optionally include a minimum amount of a short chain alcohol or acetone, and reacting the obtained ester with molecular para-hydrogen, in the presence of a catalyst soluble into the organic solvent but water insoluble, to give the corresponding para-hydrogenated ester;

b) applying an appropriate field cycling procedure to the obtained parahydrogented ester to give the an organic solution of the corresponding [1-$^{13}$C]-hyperpolarized ester, c) diluting the organic solution of the [1-$^{13}$C]-hyperpolarized ester with a suitable aqueous solution promoting the hydrolysis of the hyperpolarized ester to the corresponding water soluble [1-$^{13}$C]-hyperpolarized carboxylate containing molecule, or the corresponding carboxylic acid, that is then extracted, e.g. by phase transfer, into the aqueous phase and directly collected as an impurity-free aqueous solution ready for use as such in in vivo application.

Interestingly, the [1-$^{13}$C]-hyperpolarized carboxylate compound obtained according to the process of the invention as an aqueous solution ready for use as such in in vivo applications, has at least 5% of polarization consenting to provide enough sensitivity in in vivo imaging. Preferably, the polarization obtained is at least 10% and, more preferably at least 15%. On the other side, the impurity-free aqueous solution of a hyperpolarized molecule obtained according to the invention are stable for a clinically acceptable period of time; in particular preferably at least 10% of this polarization is maintained at the time of the injection, which is commonly performed rightly after the preparation of the hyperpolarized carboxylate, more preferably at least about 30% polarization is maintained, most preferably at least of about 80% polarization is maintained.

To this extent, it will be clear that the polarization method herein proposed should be carried out within the frame of time in which the hyperpolarised carboxylate molecule remains significantly polarised, shortly after being subjected to the chemical conversion (e.g. hydrolysis) of the precursor. Therefore, the administration of such active substrate and the subsequent MR measurement are preferably effected as rapid as feasible. This means that the sample, either human or non-human animal body, should be available close to the area in which the polarisation takes place.

Aqueous solutions according to the instant invention preferably include the hyperpolarized molecule of interest in a concentration ranging between 0.002 and 1.0 M and preferably between 0.01 and 0.5 M.

The impurity-free aqueous solution of a hyperpolarized molecule obtained, for instance, according to the step d) or, more preferably, as above said, directly collected from the step c) of the process, according to a particularly preferred embodiment of the invention, finds advantageous use as such, (i.e. without further purification and/or subsequent formulation) in in vitro, ex vivo and, especially, in vivo MR diagnostic imaging of a human or animal body organ, fluid, region or tissue, as well as for the diagnostic assessment of physiological parameters of diagnostic interest in an individual, human or animal, patient.

Even preferably, they may find advantageous use in the emerging field concerning the evaluation of metabolic profiles of diagnostic interest in an individual patient by use of MR imaging techniques. In particular, the assessment of the metabolic conversion of a concerned hyperpolarized carboxylate may allow to provide an evaluation of the metabolic processes in an individual patient and/or information on metabolic state of a (healthy or pathological) patient's tissue or organ.

Accordingly, in an additional embodiment, the instant invention relates to a MR contrast agent that is characterized in that it comprises, or, preferably, consists of the impurity-free aqueous solution of the [1-$^{13}$C]-hyperpolarized carboxylate compound collected according to step d) or, more preferably, directly collected from step c) of the process, according to a particularly preferred embodiment of the invention.

In a particularly preferred embodiment, the said [1-$^{13}$C]-hyperpolarized carboxylate compound is the [1-$^{13}$C]-hyperpolarized lactate.

In an alternative, equally preferred, embodiment the said [1-$^{13}$C]-hyperpolarized carboxylate compound is the is the [1-$^{13}$C]-hyperpolarized acetate.

In an especially preferred embodiment, the [1-$^{13}$C]-hyperpolarized carboxylate compound according to the invention is the [1-$^{13}$C]-hyperpolarized pyruvate.

The invention moreover relates to a Para-Hydrogen Induced Polarization process that in addition to process steps from a) to c) or from a) to d), allowing to get an impurity-free aqueous solution of the [1-$^{13}$C]-hyperpolarized carboxylate molecule of interest as above described, further comprises employing the collected aqueous solution for the MR diagnostic imaging of an individual patient or for the in vivo or in vitro, ex vivo, MR assessment of biological parameters or metabolic profiles of diagnostic interest.

More particularly, according to a further embodiment, the invention relates to a Para-Hydrogen Induced Polarization process that comprises:
 i) collecting an aqueous solution of a [1-$^{13}$C]-hyperpolarized molecule of interest according to step d) or, more preferably, directly from the step c) of a process according to the invention, as above described, the said process, in addition, further comprises:
 ii) administering the collected aqueous solution of the [1-$^{13}$C]-hyperpolarized carboxylate molecule of interest to an individual patient, or contacting the said aqueous solution with an ex vivo sample of a body organ, fluid or tissue of an individual patient;
 iii) exposing the administered individual patient (or ex vivo sample) to a radiation frequency allowing to excite the hyperpolarized $^{13}$C-labeled carbon atom of the carboxylate molecule;
 iv) recording the signal intensity generated by the excited nucleus of the administered carboxylate molecule and/or of any suitable metabolite or catabolite thereof, and
 v) obtaining an image of the individual patient body organ, region or tissue, or suitable estimates of the biological parameter or metabolic profile of interest from recorded signal intensity values.

To this extent, the steps of the above process including exposing the administered patient or ex vivo sample to an appropriate exciting radiation, recording the signal intensity generated by the excited nucleus, and obtaining an image of the individual patient body organ, region or tissue, or suitable estimates of the biological parameter or metabolic profile of interest from recorded signals intensity values can be suitably carried out according to conventional techniques and operative procedures well known to those skilled in the relevant art.

The invention moreover relates to a method for the in vivo diagnostic MR imaging of a body organ, region, fluid or tissue or for the in vivo or in vitro, ex vivo, MR assessment of biological parameters or metabolic profiles of diagnostic interest in an individual patient that comprises:
 i) collecting an aqueous solution of the a [1-$^{13}$C]-hyperpolarized carboxylate molecule of interest according to the process of the invention, e.g. from step d) or, more preferably, directly from step c) of the process, as formerly disclosed;
 ii) administering the said collected aqueous solution to the individual patient, or contacting the said aqueous solution with an ex vivo sample of a body organ, fluid or tissue of the individual patient;
 iii) exposing the administered patient, or the contacted ex vivo sample to a radiation frequency allowing to excite the hyperpolarized $^{13}$C-labeled carbon atom of the carboxylate molecule;
 iv) recording the signal intensity generated by the excited nucleus of the administered carboxylate molecule and/or of any suitable metabolite or catabolite thereof; and
 v) obtaining an image of the individual patient body organ, region or tissue, or suitable estimates of the biological parameter or metabolic profile of interest from recorded signals intensity values.

The above method may alternatively comprises exposing to a radiation frequency exciting the $^{13}$C-hyperpolarized carboxylate molecule a patient pre-treated with a proper amount of aqueous solution of the a [1-$^{13}$C]-hyperpolarized carboxylate molecule, and the recording the signal intensity generated by the excited $^{13}$C-nucleus or, still alternatively, it can includes obtaining signal intensity values (and, in turn, estimates of biological parameters or metabolic profiles of diagnostic interest) from a collection of MRI signals acquired, at the appropriate time, by an individual patient properly treated with an effective amount of aqueous solution of the a [1-$^{13}$C]-hyperpolarized carboxylate molecule and suitably exposed to a radiation frequency allowing to excite the hyperpolarized $^{13}$C-signal of the carboxylate molecule, and then digitally stored in the tomograph's console memory, or in a local or remote digital data storage device.

In this respect, unless otherwise indicated, with "individual patient" or "patient" as used herein we refer to a human or animal patient, and, preferably a human being undergoing MR diagnostic assessment.

On the other side, with "effective amount" or "suitable amount", as herein used interchangeably, we refer to any amount of the aqueous solution of the hyperpolaryzed molecule collected according to the process of the invention and, preferably, directly collected from step c) of the preferred process implementation that is sufficient to fulfil its intended diagnostic purpose(s): i.e., for example, to acquire the signal generated by the excited nucleus of the administered carboxylate molecule and/or of any suitable metabolite or catabolite thereof.

To this end, the impurity-free aqueous solution of the [1-$^{13}$C]-hyperpolarized carboxylate (or carboxylic acid) obtained by use of the method of the present invention can be administered as such into the vascular system or directly into an organ or muscle tissue, or by subdermal or subcutaneous route, as the case may be. Then, according to the present method, the sample is exposed to a uniform magnetic field (also known as "primary magnetic field") with radiation of a frequency selected to excite nuclear spin transitions in the said hyperpolarised $^{13}$C-carboxylic signal. The hyperpolarization of the $^{13}$C-signal of the carboxylic ester and, consequently, of the corresponding carboxylate molecule, results in an increasing in the population difference between the excited and ground nuclear spin states of those nuclei which are responsible for the magnetic resonance signals. Since MR signal intensity is proportional to this population difference, the final detected MR signals result in larger amplitude signals. The amplitude of the induced MR signals is also dependent upon several other factors, such as the strength of the magnetic field, the temperature of the sample, the isotopic nature and chemical environment of the imaging nuclei and the like.

The present invention will be further illustrated by the following examples that are intended to be illustrative and are in no way limiting the scope of the invention.

Experimental Part

All the $^{13}$C-NMR spectra are acquired into a 600 MHz Bruker spectrometer, by operating at 14.1 T, and 298 K.

EXAMPLES

All the chemicals and reagents used are commercially available or can be prepared according to well-known methods of the art.

Example 1

Preparation of [1-$^{13}$C]-Hyperpolarized Acetate from Vinyl Ester: [1-$^{13}$C]-Hyperpolarization Carried Out in an Aqueous Medium

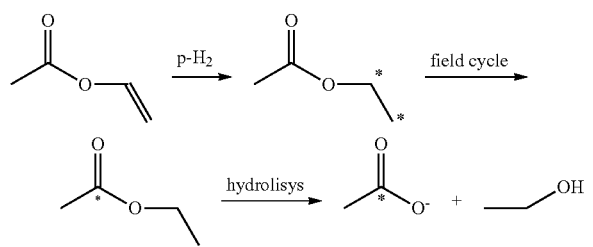

The Parahydrogenation of Vinyl-Acetate

The parahydrogenation of vinyl-acetate (purchased by Sigma-Aldrich; reference code V1505) has been carried out in water using the water soluble catalyst [Rh(NBD)phos][BF$_4$] (NBD=norbornadiene, phos=1,4-bis[(phenyl-3-propane sulfonate)phosphine]butane disodium salt) (2.5 mM deuterated water solution) (this catalyst can be prepared e.g. according to the procedure reported in Magn. Reson. Mat. Phys. Biol. Med. 22, 123-34 (2009). The parandyrogenation reaction has been carried out into a NMR tube equipped with Young valve charged with 0.3 ml of catalyst, 0.03 mmol of substrate (3 μl, final concentration about 100 mM), 0.05 ml of methanol and 8 bar of parahydrogen (enriched at 77K, 50% enrichment).

Preparation of the [1-$^{13}$C]-hyperpolarized Ethyl Ester

After warming the solution at 90° C., the NMR tube was vigorously shaken for 10", then the 13C spectrum has been immediately acquired. In FIG. 2 it can be observed that hyperpolarization is only on the aliphatic 13C signals. An experiment was then repeated as above described, in which after shaking the NMR tube, a field cycling was applied. In practical terms, the NMR tube was dropped into a μ-metal magnetic field shield, then slowly extracted from the shield in about 5". The $^{13}$C-NMR spectrum was then immediately acquired (of the obtained solution) with a 600 MHz Bruker spectrometer. FIG. 3a reports recorded 13C-NMR spectrum showing the hyperpolarized $^{13}$C-carboxylate resonance of the formed [1-$^{13}$C]-hyperpolarized ethyl ester at 176 ppm.

Preparation of the [1-$^{13}$C]-hyperpolarized Acetate

To get the corresponding [1-$^{13}$C]-hyperpolarized acetate, the para-hydrogenation reaction has repeated as above described with a second amount of vinyl-acetate. The obtained [1-$^{13}$C]-hyperpolarized ester is then hydrolysed by addition of 0.05 ml of NaOD 6M immediately after field cycling procedure and a 13C-NMR spectrum is then acquired. FIG. 3b) reports the 13C-NMR spectrum of the obtained acetate, as sodium salt in which the $^{13}$C-hyperpolarized signal of the acetate is detectable at 181 ppm. Interestingly, the attained polarized signal intensity is well comparable with the one observed for the parent ethyl acetate shown in FIG. 3a).

Example 2

Preparation of [1-$^{13}$C]-hyperpolarized Acetate from the Propargyl Ester: [1-$^{13}$C]-hyperpolarization Carried Out in an Aqueous Medium Synthesis of Propargyl Acetate

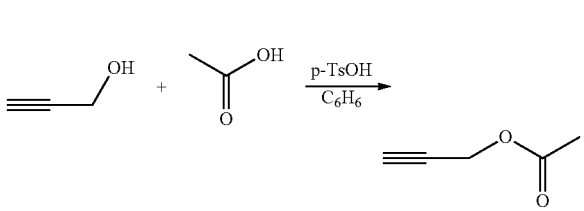

Acetic acid (2.00 g, 34.1 mmol) and propargyl alcohol (2.29 g, 40.9 mmol) were heated for 4 h at reflux in C$_6$H$_6$ (120 cm$^3$) in the presence of a catalytic amount of p-TsOH (0.32 g, 1.7 mmol) using a Dean-Stark apparatus. The reaction was allowed to cool to room temperature and was washed with saturated NaHCO$_3$ (2×100 mL) and then with water (2×100 mL). The organic layer was collected and dried (with anhydrous Na$_2$SO$_4$), filtered and concentrated to yield the crude product as an odorless mobile yellow oil (1.67 g, 50%) which was used without further purification.

Preparation of the [1-$^{13}$C]-hyperpolarized Acetate

The parahydrogenation reaction of the obtained propargyl ester has been carried out in an hydroalcoholic medium as formerly described in Example 1 for the acetate molecule and as schematized in scheme b) of FIG. 1 (where R is CH$_3$). After application of field cycling, carried out as formerly described in Example 1, a $^{13}$C-polarization of the carboxylate carbon atom is obtained comparable to that observed with the vinyl ester, respectively before (FIG. 3c) and after (FIG. 3d) hydrolysis, carried out, this latter, as formerly described in example 1.

Example 3

Preparation of [1-$^{13}$C] Hyperpolarizd Pyruvate from Propargyl Ester: [1-$^{13}$C]-hyperpolarization Carried Out in an Aqueous Medium and in Methanol/CDCl$_3$ Synthesis of Propargyl Pyruvate

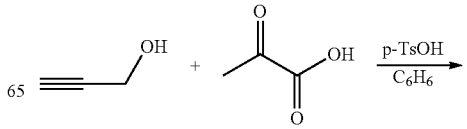

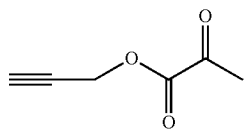

Pyruvic acid (3.00 g, 34.1 mmol) and propargyl alcohol (2.29 g, 40.9 mmol) were heated for 4 h at reflux in $C_6H_6$ (120 cm$^3$) in the presence of a catalytic amount of p-TsOH (0.32 g, 1.7 mmol) using a Dean-Stark apparatus. The reaction was allowed to cool to room temperature and was washed with sat. NaHCO$_3$ (2×100 mL) and then with water (2×100 mL). The organic layer was collected and dried (anh. Na$_2$SO$_4$), filtered and concentrated to yield the crude product as an odorless mobile yellow oil (2.08 g, 49%) which was not purified further.

Preparation of the [1-$^{13}$C]-hyperpolarized Pyruvate

Preparation of the [1-$^{13}$C]-hyperpolarized Allyl-Ester in Aqueous Medium

The parahydrogenation of the propargyl-pyruvate has been carried out in an hydro-alcoholic hydrogenation medium (15% methanol in water) using the water soluble catalyst [Rh(NBD)phos][BF$_4$] (2.5 mM deuterated water solution).

The parandyrogenation reaction has been carried out into a NMR tube equipped with Young valve charged with 0.3 ml of catalyst, 0.03 mmol of substrate (3 µl, concentration about 70 mM), 0.05 ml of methanol and 8 bar of parahydrogen (enriched at 77K, 50% enrichment).

After warming the solution at 90° C., the NMR tube was vigorously shaken for 10", then was dropped into a µ-metal magnetic field shield and successively slowly extracted from the shield in about 5". The $^{13}$C-NMR spectrum has then been immediately acquired into a 600 MHz Bruker spectrometer. [1-$^{13}$C]-hyperpolarized allyl pyruvate is obtained as schematized in FIG. 1, scheme b, where R═CH$_3$—CO.

Figure 4:
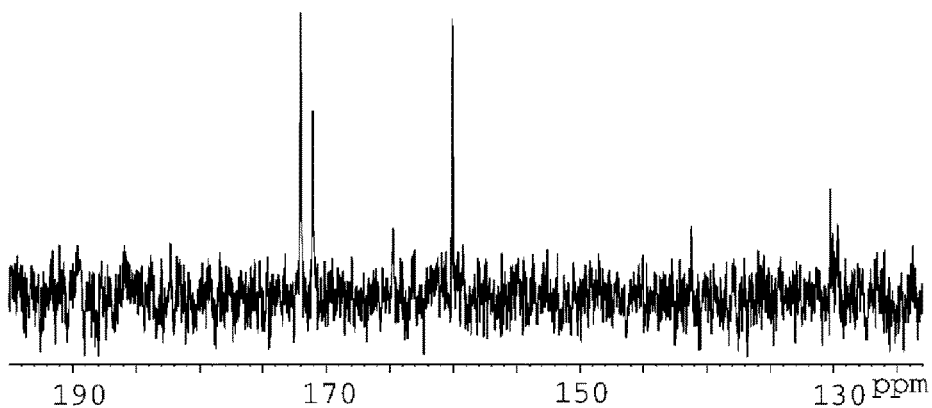
FIG. 4. $^{13}$C carbonyl signals of parahyrogenation products of propargyl pyruvate after field cycling. The parahydrogenation is carried out in water added with 15% methanol. Three signals in the carbonylic region are clearly detectable due to pyruvate allyl-ester (160 ppm: structure a) in the figure, the hydrate form (172 ppm: structure b) in the figure) and the emiacetal (171 ppm: structure c) in the figure).
Figure 4:
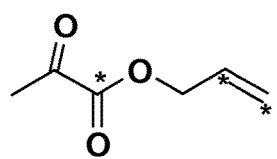
Figure 4:
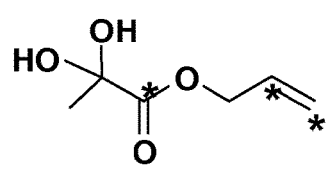
Figure 4:
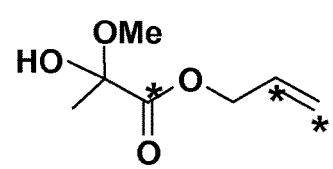

In the $^{13}$C spectrum acquired immediately after application of field cycling (shown in FIG. 4) three signals in the carbonylic region are clearly visible, ascribable to pyruvate allyl-ester (160 ppm: structure a) of FIG. 4), the hydrate form (172 ppm: structure b)) and the emiacetal (171 ppm: structure c)). The last species is due to the presence of 15% methanol in water, added to facilitate dissolution of the substrate in water and to improve catalyst efficiency, which promotes its formation.

Preparation of the [1-$^{13}$C]-hyperpolarized Allyl-Ester in Methanol

The parandyrogenation reaction has then been carried out in methanol, as reaction solvent, using the commercial catalyst [Rh(COD)dppb][BF$_4$] (COD=cyclo-1,5-octadiene, dppb=1,4-bis(diphenylphosphino)butane). The parahydrogenation reaction has been carried out into a NMR tube equipped with Young valve charged with 2 mg of catalyst and 0.4 ml of methanol-d$_3$. The catalyst was activated by hydrogenation of the coordinated COD, then 3 µl of substrate were added and the NMR tube was pressurized with 8 bar of parahydrogen (enriched at 77K, 50% enrichment).

Figure 5:
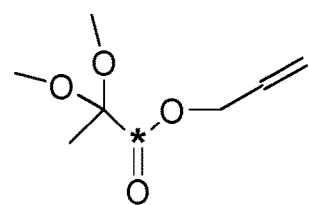
FIG. 5. acetalic form of the pyruvate in methanol.
Figure 6:
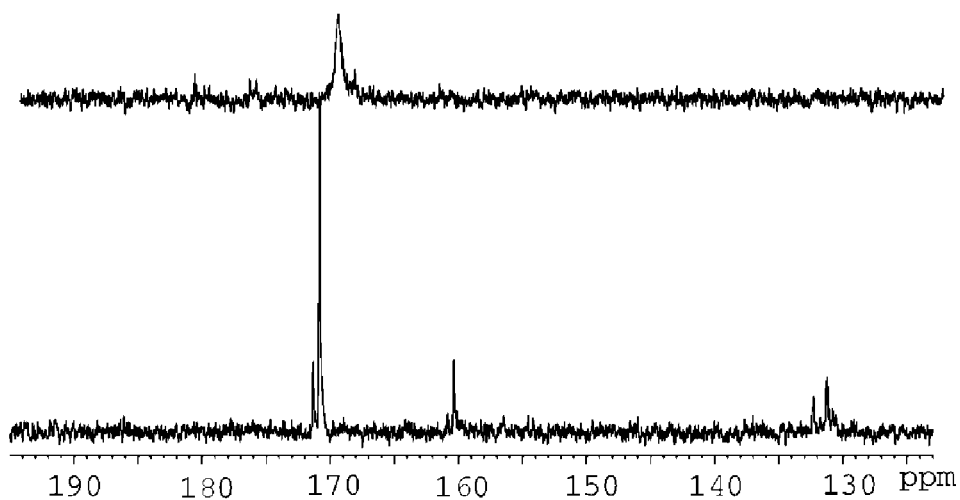
FIG. 6. a) $^{13}$C hyperpolarized signal provided by the parahydrogenated propargyl pyruvate in methanol: the most intense signal corresponds to the acetalic form in the methanol medium; b) $^{13}$C hyperpolarized signal after addition of 200 μl of NaOD 1M.

After warming the solution at RT, the NMR tube was vigorously shaken for 10", magnetic field cycling was applied as described in example 1 and then the 13C spectrum has been acquired. As can be observed from recorded spectrum, shown as FIG. 6, most of the polarized product is due to the acetalic form of pyruvate, having the structure of FIG. 5.

Preparation of the [1-$^{13}$C]-hyperpolarized Allyl-ester in Methanol/CDCl$_3$

The parahydrogenation reaction of the propargyl-pyruvate was then carried out in an organic medium consenting to benefit from a phase transfer-extraction of the [1-$^{13}$C]-hyperpolarized pyruvate, allowing to remove the hydrogenation catalyst and to reduce to substantially non-detectable values the amounts of optional alcoholic (or water miscible) co-solvents in the final aqueous mixture, thereby leading to a substantially impurity-free aqueous solution of the desired [1-$^{13}$C]-hyperpolarized pyruvate.

More particularly, the parahydrogenation reaction of the propargyl-pyruvate was carried out in a methanol/CDCl$_3$ mixture (75 µl methanol and 500 µl CDCl$_3$) with the commercial [Bis(diphenylphosphinobutane)(1,5-cyclooctadiene)]Rh(I) as hydrogenation catalyst. The parahydrogenation reaction has been carried out into a NMR tube equipped with Young valve charged with 2 mg of catalyst and 0.05 ml of methanol-d$_3$. The catalyst was activated by hydrogenation of the coordinated diene, then CDCl3 and the substrate (3 µl of the propargyl ester in 25 µl of methanol) were added, the tube was pressurized with 8 bar of para-H2. After warming the solution at 90°, the NMR tube was vigorously shaken for 10" to give the parahydrogenated intermediate of FIGS. 10 (1H-NMR spectrum) and 11 (13C-NMR spectrum) in the acetalic form (due to the methanol in solution). The experiment was then repeated as above described with a second amount of propargyl pyruvate in which, after warming the solution at 90° and shaking the NMR tube for 10", a magnetic field cycling was applied as described in example 1, leading to get the [1-$^{13}$C]-hyperpolarized ester. The basic hydrolysis of the hyperpolarized ester was then carried out by addition of 0.5 ml of NaOD 1M to the reaction mixture maintained at about 90° C. Preferably, the addition is performed by rapid injection of the aqueous solution of NaOD through the organic phase, thereby obtaining the desired fastest mixing of the two organic and aqueous phases.

The obtained basic solution was then brought to acidic pH (pH 4) by addition of 0.5 ml DCl. The aqueous phase was then collected and a $^{13}$C spectrum is immediately recorded shoving the $^{13}$C polarized signal of the pyruvate (FIG. 7, spectrum c)) at around 168 ppm, impurity free.

In order to may use the collected aqueous solution of hyperpolarized pyruvate in in vivo applications it is necessary that the aqueous solution is suitably buffered at a physiological pH (pH~7). However, the basic solution of the hyperpolarized pyruvate (obtained after addition of NaOD (1M)) is, preferably first acidified to acidic pH, for instance by addition of DCl, as above said, consenting to restore the methyl group of the pyruvate molecule from α-deprotonated pyruvate and its corresponding hydrate form optionally formed at basic (pH>8) hydrolytic conditions. Then, the acidic solution is suitably buffered at pH~7, for instance with phosphate buffer 0.1 M, thereby obtaining an impurity free, and physiologically acceptable solution of the hyperpolarized pyruvate ready for use in in vivo applications.

Example 4

Preparation of [1-$^{13}$C] Hyperpolarized TFA-Glycine Ethyl Ester: [1-$^{13}$C]-hyperpolarization Carried Out in MeOH and in Acetone a) Synthesis of the Substrate Molecules i) 2-(2,2,2-trifluoroacetamido)acetic acid (Prepared as Described in Tetrahedron, 2003, 59, 9019-9029)

To a stirred suspension of 2 g (25.5 mmol) of glycine in 6 mL of a 30% w/w solution of sodium methoxide in methanol, 10 mL (51.10 mmol) of ethyl trifluoroacetate were slowly added at 0° C. Then temperature was slowly increased to room temperature and the solution was stirred for 4 hours. Then methanol was evaporated and the residue was partitioned between aqueous HCl 1M and diethyl ether. The organic phase was extracted with diethyl ether (2×100 mL) and the combined organic layers were washed with brine (3×100 mL), dried over Na$_2$SO$_4$ and the solvent was evaporated under reduced pressure. A white solid was obtained (3.61 g, 79%) and it was used with no further purification.

NMR characterization: $^1$H NMR (acetone-d$_6$ 400 MHz) d 8.90 (1H, bs, NH), 4.06 (2H, d, J=5.86 Hz, CH$_2$)

$^{13}$C NMR (acetone-d$_6$, 100 MHz) d 169.7 [C, COOH], 158.0 [C, q, $^2$J$_{C-F}$=36.8 Hz, COCF$_3$], 117.0 [C, q, J$_{C-F}$=285.3 Hz, COCF$_3$] 41.4 [CH$_2$].

$^{19}$F NMR (acetone-d$_6$ 376 MHz) d −76.44 ii) vinyl 2-(2,2,2-trifluoroacetamido)acetate (TFA-Gly-OVinyl) (Prepared as Disclosed for Instance in Org. Process Research and Development, 2009, 13, 706-709

To a stirred suspension of the intermediate compound obtained from step i) (1.30 g, 7.60 mmol) in 15 mL of vinyl acetate, Pd(OAc)$_2$ (0.02 g, 0.08 mmol) and KOH (0.04 g, 0.76 mmol) were added under argon atmosphere. The solution was stirred overnight at room temperature. The mixture was then quenched with water and diethyl ether was added. The aqueous phase was extracted with diethyl ether (2×50 mL), washed with brine (3×50 mL), dried over Na$_2$SO$_4$, filtered and the solvent was evaporate. The crude reaction was then purified on silica gel using diethyl ether/petroleum ether (40/60) as eluent to afford the desired product as a pale yellow solid (0.37 g, 25%).

NMR characterization:

$^1$H-NMR (acetone-d$_6$ 400 MHz) d 9.00 (1H, s, NH), 7.26 (1H, dd J$_{cis}$=6.16 Hz, J$_{trans}$=13.76 Hz CH), 4.93 (1H, J$_{trans}$=13.76 Hz, CH$_2$), 4.68 (1H, d, J$_{cis}$=6.16 Hz, CH$_2$), 4.25 (2H, d, J=4.25, CH$_2$)

$^{13}$C-NMR (acetone-d$_6$, 100 MHz) d 166.6 [C, COOVinyl], 158.3 [C, $^2$J$_{C-F}$=36.7 Hz, COCF$_3$], 141.8 [CH], 116.9 [C, J$_{C-F}$=285.2 Hz, COCF$_3$], 99.0 [CHCH$_2$], 41.5 [NHCH$_2$]

$^{19}$F NMR (acetone-d$_6$ 376 MHz EK 492) d −76.5 b) Parahydrogenation of the Trifluoro-acetyl Glycine Vinyl-ester in Acetone and Methanol.

The hydrogenation reaction of the trifluoro-acetyl vinyl-glycine 1 obtained as above described was carried out either in acetone or in methanol according to the following reaction scheme

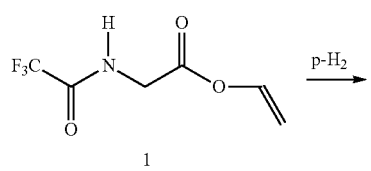

1

Figure 8:
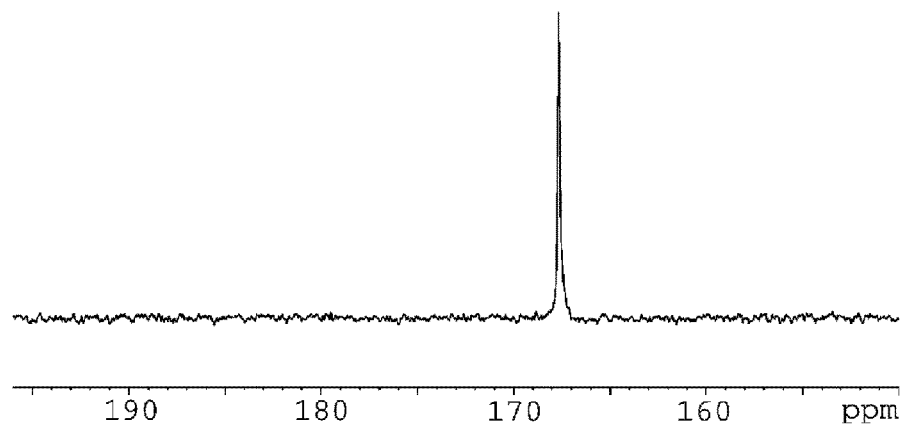
FIG. 8. $^{13}$C polarized carbonyl signal (167 ppm) of parahydrogenated TFA-ethyl glycine obtained by addition of para-hydrogen to the corresponding vinyl glycine and field cycling, in MeOH.

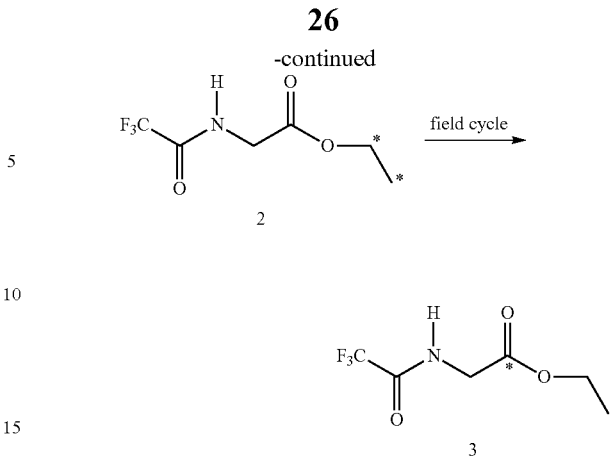

by using, with both solvents, the commercial hydrogenation catalyst [Rh(COD)dppb] and by following, in both cases, the procedure already used for preparation of the [1-$^{13}$C]-hyperpolarized allyl-ester in methanol, as described in Example 3. Following to the application of field cycle, a $^{13}$C polarized carbonyl signal (167 ppm) was observed in both solvents, as observed, for instance, in the 13C-NMR spectrum of FIG. 8 recorded from the hydrogenation reaction carried out in methanol.

Example 5

Preparation of [1-$^{13}$C] Hyperpolarized Glycine from Propargyl Ester: [1-$^{13}$C]-hyperpolarization Carried out in a Methanol/CDCl3 Mixture a) Preparation of the prop-2-ynyl 2-(2,2,2-trifluoroacetamido)acetate (TFA-Gly-OPropargyl) (Prepared According to e.g. J. Org. Chem, 2009, 74, 3406-3413)

Under argon atmosphere, 0.2 mL (3.51 mmol) of propargyl alcohol and 0.02 g (0.18 mmol) of DMAP ((Dimethylamino)pyridine) were added to a stirrer solution of compound 1 in dry dichloromethane. Temperature was decreased at 0° C. and 2.63 g (2.63 mmol) of DCC (Dicyclohexylcarbodiimide) were added. The temperature was slowly increased until room temperature and the solution as stirred for 3 hours. The white formed precipitate was filtered off and dichloromethane was evaporated under reduced pressure. The crude was purified on silica gel using diethyl ether/petroleum ether (50:50) as eluent affording 0.25 g (68%) of the desire product as a white solid.

NMR characterization:

$^1$H-NMR (acetone-d$_6$ 400 MHz, EK 473) d 8.89 (1H, bs, NH), 4.79 (2H, d, J$^4$=2.36 Hz, COOCH$_2$), 4.17 (2H, d, J=5.88, NHCH$_2$), 3.05 (1H, t, J$^4$=2.36 Hz, CH)

$^{13}$C-NMR (acetone-d$_6$, 100 MHz, EK 473) d 168.4 [C, COO-propargyl], 158.3 [C, $^2$J$_{C-F}$=36.7 Hz, COCF$_3$], 116.9 [C, q, J$_{C-F}$=285.2 Hz, COCF$_3$], 78.2 [C, CCH], 76.8 [CH, CCH], 53.3 [CH$_2$, COOCH$_2$], 41.5 [CH$_2$, NHCH$_2$]

$^{19}$F NMR (acetone-d$_6$ 376 MHz EK 492) d −76.4 b) Preparation of an Impurity Free Aqueous Solution of the [1-$^{13}$C]-hyperpolarized-glycine

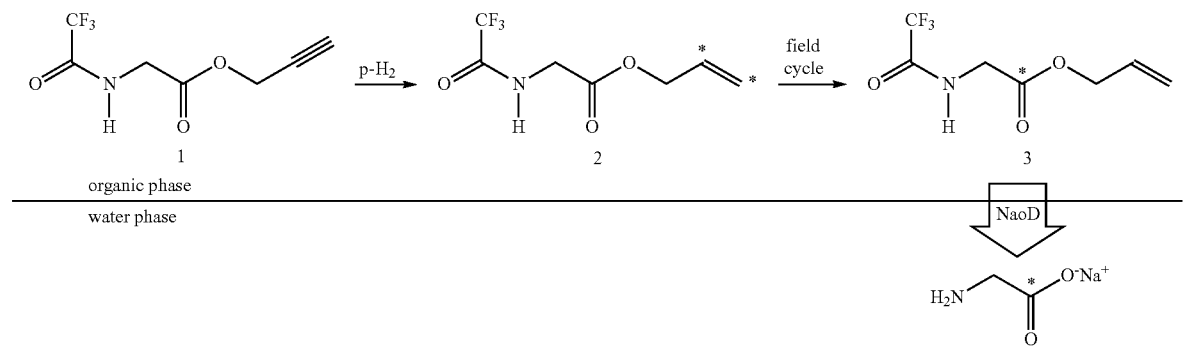

Reaction scheme:

The parandyrogenation of the obtained TFA-Gly-OPropargyl 1 has been carried out using the commercial catalyst [Rh(COD)dppb] in a Methanol/CDCl3 mixture (200µ/500 µl) using the same procedure described in Example 3 for the preparation of the [1-$^{13}$C]-hyperpolarized allyl-ester in methanol/CDCl$_3$, with 200 µl of methanol-d$_3$ instead of 75 µl. Following to the application of field cycle, the hydrolysis of the [1-$^{13}$C]-hyperpolarized TFA-Gly-OAllyl ester has been performed by the addition of 1 ml NaOD 2M consenting to remove both the hydrogenated ester moiety (namely allyl-alcohol) and the protecting group TFA (trifluoroacetic acid). A 13C-NMR spectrum of the directly collected aqueous phase was then recorded, shown in FIG. 9. A $^{13}$C polarized signal is observed in the recorded spectrum at 181 ppm, corresponding to the [1-$^{13}$C]-hyperpolarized free glycine, impurity free. Interestingly, despite being recorded on the aqueous phase directly collected after hydrolysis of the hydrogenated ester and phase transfer extraction of the [1-$^{13}$C]-hyperpolarized glycine, the recorded spectrum is devoid of any detectable impurity, including any instrumentally detectable residue of the methanol used as hydrogenation co-solvent.

Example 6

Preparation of [1-$^{13}$C] Hyperpolarized Lactate in an Aqueous Medium a) Preparation of the Substrate Molecule 2-acetoxy-propionic Acid Vinyl Ester (Vinyl-lactate)

To a stirring suspension of 2-Acetoxy-propionic acid (3.0 g, 23 mmol) in 66 mL of vinyl acetate, Pd(OAc)$_2$ (0.076 g, 0.34 mmol) and KOH (0.200 g, 3.5 mmol) were added under nitrogen atmosphere. The solution was stirred for 48 hours at room temperature. The mixture was then quenched with water, the catalyst was filtered and diethyl ether was added. The aqueous phase was extracted with diethyl ether (3×40 mL), washed with brine (3×50 mL), dried over Na$_2$SO$_4$, filtered and the solvent was evaporate. The crude was then purified on silica gel using diethyl ether/petroleum ether (1/4) as eluent to afford the desired product as a pale yellow oil (0.579 g, 16%).

$^1$H-NMR (CDCl$_3$ 400 MHz) 7.2 (1H, dd, CH$_2$), 5.1 (1H, q, CH) 4.95 (1H, d CH), 4.65 (1H, d CH$_2$), 2.12 (3H, s, CH$_3$), 1.5 (3H, d, CH$_3$).

$^{13}$C-NMR (CDCl$_3$, 100 MHz) d 171 [C, COOVinyl], 168[C, COOCH$_3$], 141 [CH], 100 [CHCH$_2$], 67 [CH], 20 [CH$_3$], 17 [CH$_3$]

b) Preparation of the [1-$^{13}$C]-hyperpolarized Ethyl Lactate

Reaction scheme:

The parahydrogenation of 2-Acetoxy-propionic acid vinyl ester (1) has been carried out in water with the water soluble catalyst [Rh(NBD)phos][BF$_4$] according to the same procedure reported in Example 1 for the preparation of the [1-$^{13}$C]-hyperpolarized ethyl ester of acetate, using 0.05 ml of acetone instead of methanol.

Figure 12:
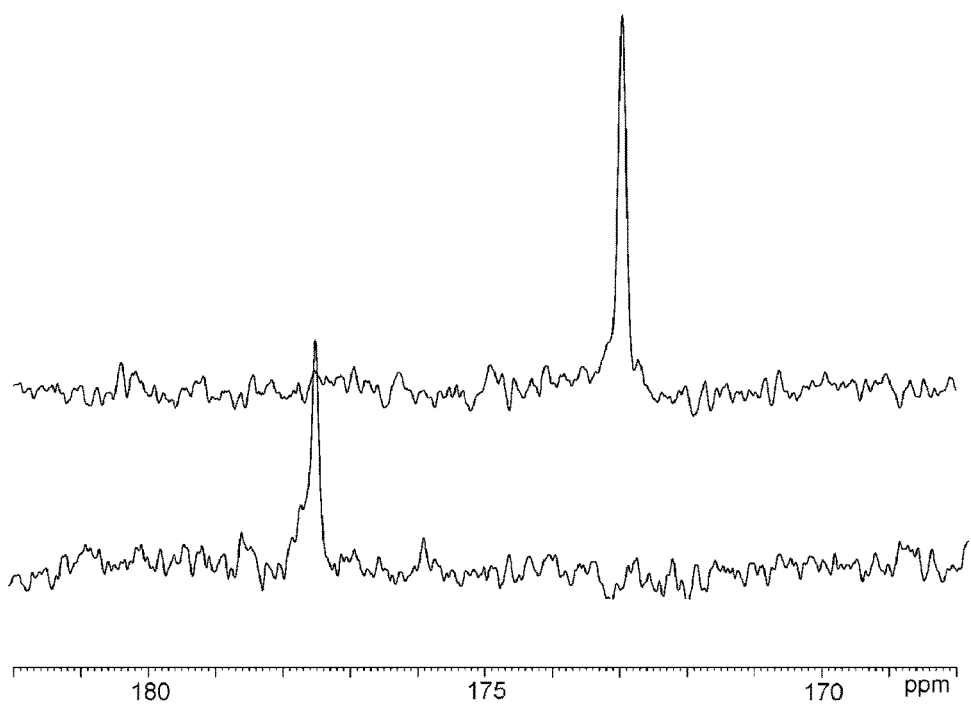
FIG. 12. $^{13}$C-NMR spectra (14 T, 298 K, D$_2$O) of $^{13}$C hyperpolarized ethyl lactate after para-hydrogenation of the vinyl-ester and field cycling (upper spectrum) and after subsequent hydrolysis of the hyperpolarized ester (lower spectrum). In the upper spectrum, the $^{13}$C polarized carbonyl signal of 2-acetoxy-propionic acid ethyl ester (3) is detectable at 173 ppm; in the lower spectrum the $^{13}$C-hyperpolarized signal of [1-$^{13}$C]-hyperpolarized lactate is detectable at 177.5 ppm.

Following to the application of magnetic field cycling, a $^{13}$C polarized carbonyl signal (173 ppm) of 2-Acetoxy-propionic acid ethyl ester (3) was observed (FIG. 12 upper spectrum).

c) Preparation of the [1-$^{13}$C]-hyperpolarized lactate

To get the corresponding [1-$^{13}$C]-hyperpolarized lactate, the para-hydrogenation reaction is repeated as above described with a second amount of vinyl ester (1) and the obtained [1-$^{13}$C]-hyperpolarized ester is hydrolysed by addition of 0.05 ml of NaOD 12M immediately after field cycling procedure. The obtained solution is then acidified by the addition of 0.05 ml of DCl 12M and a 13C-NMR spectrum is immediately acquired. FIG. 12 (lower part)

reports the 13C-NMR spectrum of the obtained lactate, in which the $^{13}$C-hyperpolarized signal of lactate is detectable at 177.5 ppm.

The invention claimed is:

1. A Para-Hydrogen Induced Polarization process for the preparation of an [1-$^{13}$C]-hyperpolarized carboxylate containing molecule comprising hydrogenating with molecular para-hydrogen an unsaturated alkenyl or alkynyl ester of said carboxylate containing molecule of formula (II)

    (II)

in which:
C* denotes the naturally $^{13}$C enriched or, optionally, $^{13}$C labeled carboxylate carbon atom undergoing $^{13}$C hyperpolarization;
R' is an allyl of formula —CH$_2$—CH=CH$_2$ or a propargyl residue of formula —CH$_2$—C≡CH;
R is a C$_1$-C$_5$ linear or branched alkyl chain, which is optionally interrupted by, or substituted with, one or more groups selected from the group consisting of carbonyl (—CO—), hydroxyl (—OH), amino (—NHR$_1$), halogen atom, halo-alkyl group, carbocyclic aliphatic moiety optionally substituted by one or more hydroxyl groups, and aromatic moiety optionally substituted by one or more hydroxyl groups; and
R$_1$ is H or an amino protecting group, or a physiologically acceptable salt thereof.

2. A process according to claim 1, wherein R is selected from the group consisting of C$_1$-C$_5$ alkyl, methylcarbonyl, hydroxyethyl, and aminoalkyl of formula R$_2$—CH(NHR$_1$)—, in which R$_1$ is H or an amino protecting group selected from the group consisting of trifluoroacetyl, acetyl, benzoyl, carbobenzoxy, and tert-butyl carbonate, and R$_2$ is H or C$_1$-C$_4$ alkyl chain optionally substituted by a hydroxyl group, a phenyl ring, or a hydroxyphenyl ring.

3. A process according to claim 2, wherein R is methyl.

4. A process according to claim 2, wherein R is methylcarbonyl.

5. A process according to claim 2, wherein R is an aminoalkyl of formula R$_2$—CH(NHR$_1$)—.

6. A process according to claim 2, wherein R is a hydroxyethyl of formula CH$_3$CH(OH)—.

7. A process according to claim 1, comprising:
a) obtaining the unsaturated alkenyl or alkynyl ester of the carboxylate containing molecule of interest and reacting said unsaturated ester with the molecular para-hydrogen to produce a para-hydrogenated ester with an [1-$^{13}$C]-carboxylate carbon atom and added polarized hydrogen;
b) inducing a polarization transfer from the added polarized hydrogen to the [1-$^{13}$C]-carboxylate carbon atom of the para-hydrogenated ester to produce an [1-$^{13}$C]-hyperpolarized ester; and
c) hydrolyzing the [1-$^{13}$C]-hyperpolarized ester and collecting an aqueous solution of the [1-$^{13}$C]-hyperpolarized carboxylate containing molecule, or of the corresponding [1-$^{13}$C]-hyperpolarized carboxylic acid.

8. A process according to claim 7, wherein the step a) comprises reacting the unsaturated ester with molecular para-hydrogen in an aqueous solvent, optionally including an amount from 10% to 30% of an organic solvent selected from short-chain alcohol or acetone, and in the presence of a water soluble hydrogenation catalyst.

9. A process according to claim 8, wherein the hydrogenation catalyst is selected from the group consisting of Rhodium complexes of formula [Rh(diphosphine)diene)]$^+$[anion]$^-$; where the diphosphine is a chelating phosphine selected from the group consisting of (1,4-Bis(R$_1$R$_2$)ethane) and (1,4-Bis(R$_1$R$_2$)butane), in which R$_1$ and R$_2$ are each individually selected from the group consisting of DPPETS, DPPBTS, DAPBTS, sulfonated CHIRAPHOS, and sulfonated BINAP; and where the diene is selected from the group consisting of 1,5-cyclooctadiene and norbornadiene.

10. A process according to claim 7, wherein step a) comprises reacting the unsaturated ester with molecular para-hydrogen in an organic solvent, or a suitable mixture of organic solvents, and in the presence of a hydrogenation catalyst soluble in the organic solvent and insoluble in an aqueous solvent.

11. A process according to claim 10, wherein the hydrogenation catalyst is selected from the group consisting of Rhodium complexes of formula [Rh(diphosphine)diene)]$^+$[anion]$^-$, where the diphosphine is selected from the group consisting of 1,4-Bis(diphenylphosphino)butane; 1,2-Bis(diphenylphosphino)ethane; 2,2'-Bis(diphenylphosphino)-1,1'-binaftyl; 2,3-diphenylphosphinobutane; 1,4-Bis(diphenylphosphino)-1,4-bisdeoxy-2,3-O-isopropyliden-L-treitol; and 1,2-Bis[(2-methoxyphenyl)(phenilphosphino)]ethane; and where the diene is selected from the group consisting of 1,5-cyclooctadiene and norbornadiene.

12. A process according to claim 10, wherein the organic solvent is an organochlorinated solvent selected from the group consisting of chloroform, dichloromethane, carbon tetrachloride and mixtures thereof, and mixtures of these solvents with an amount from 10% to 30% of a short-chain alcohol or acetone, and wherein the hydrogenation catalyst is [Rh(COD)dppb][BF$_4$] where COD is cyclo-1,5-octadiene and dppb is 1,4-bis(diphenylphosphino)butane).

13. A process according to claim 7, wherein the step b) is carried out by applying a field cycling procedure to the para-hydrogenated ester obtained at step a) of the process to give the corresponding [1-$^{13}$C]-hyperpolarized ester.

14. A process according to claim 10, wherein the step c) is carried out by diluting the organic solution of the [1-$^{13}$C]-hyperpolarized ester obtained at step b) with an aqueous solution promoting the hydrolysis of the ester to the corresponding water soluble [1-$^{13}$C]-hyperpolarized carboxylate containing molecule, or the corresponding carboxylic acid, and then collecting, by phase transfer extraction, the aqueous solution of the [1-$^{13}$C]-hyperpolarized compound of interest, which is ready for use in an in vivo application.

15. A process according to claim 8, wherein the step c) of the process is carried out by adding to the aqueous solution of the [1-$^{13}$C]-hyperpolarized ester obtained at step b) a base promoting its hydrolysis, to give the aqueous solution of the [1-$^{13}$C]-hyperpolarized carboxylate containing molecule of interest.

16. A process according to claim 15, further comprising a step d) removing the hydrogenation catalyst and the optional organic solvent from the obtained aqueous solution, to give the aqueous solution of the [1-$^{13}$C]-hyperpolarized carboxylate containing molecule of interest ready for use in an in vivo application.

17. A method of using the unsaturated alkenyl or alkynyl ester of formula (II), as defined in claim 1, as a suitable hydrogenable substrate precursor for the preparation of the [1-$^{13}$C]-hyperpolarized carboxylate containing molecule of diagnostic interest for an MR application by use of PHIP technique.

18. A process according to claim 1, wherein R' is a propargyl residue of formula —CH$_2$C≡CH.

19. A process according to claim 1, wherein the [1-$^{13}$C]-hyperpolarized carboxylate containing molecule is pyruvate.

* * * * *